US012577615B2

(12) United States Patent
Rodi

(10) Patent No.: US 12,577,615 B2
(45) Date of Patent: Mar. 17, 2026

(54) METHODS FOR THE DETECTION OF A NUCLEIC ACID

(71) Applicant: RHODX, Inc., St. Louis, MO (US)

(72) Inventor: Charles Rodi, St. Louis, MO (US)

(73) Assignee: RHODX, Inc., St. Louis, MO (US)

( * ) Notice: Subject to any disclaimer, the term of this patent is extended or adjusted under 35 U.S.C. 154(b) by 37 days.

(21) Appl. No.: 18/016,290

(22) PCT Filed: Dec. 9, 2022

(86) PCT No.: PCT/US2022/052371
§ 371 (c)(1),
(2) Date: Jan. 13, 2023

(87) PCT Pub. No.: WO2023/107682
PCT Pub. Date: Jun. 15, 2023

(65) Prior Publication Data
US 2025/0340935 A1      Nov. 6, 2025

Related U.S. Application Data

(60) Provisional application No. 63/287,854, filed on Dec. 9, 2021.

(51) Int. Cl.
*C12Q 1/6858*      (2018.01)
*C12Q 1/6818*      (2018.01)

(52) U.S. Cl.
CPC ......... *C12Q 1/6858* (2013.01); *C12Q 1/6818* (2013.01)

(58) Field of Classification Search
CPC ............................ C12Q 1/6858; C12Q 1/6818
See application file for complete search history.

(56) References Cited

U.S. PATENT DOCUMENTS 5,916,777 A      6/1999  Kacian et al.
10,619,163 B2      4/2020  Rodi

FOREIGN PATENT DOCUMENTS

WO      2016081585 A1      5/2016

OTHER PUBLICATIONS

Ding et al., Chem. Commun. 55, 12623-12626, (Year: 2019).*
Dobosy et al., BMC Biotechnology, 11:80, 1-18 (Year: 2011).*
International Search Report and Written Opinion for PCT/US2022/052371, Mar. 20, 2023.

* cited by examiner

*Primary Examiner* — Cynthia B Wilder
(74) *Attorney, Agent, or Firm* — Gregory P. Einhorn; Greer, Burns & Crain, Ltd.

(57)      ABSTRACT

In alternative embodiments, provided are primer-based nucleic acid amplification methods capable of detecting the presence of a nucleic acid sequence including at nucleotide level resolution by means of the production of a reporter. In alternative embodiments, provided are hybridization-based nucleic acid detection methods capable of single nucleotide resolution. In alternative embodiments, provided are methods for detecting a target nucleic acid sequence in a sample, which can comprises a biological sample, and optionally the biological sample comprises a cell free nucleic acid (cfNA), optionally a cell-free DNA (cfDNA) or a cell-free RNA (cfRNA), or a circulating cell-free DNA (ccfDNA) or a circulating cell-free RNA (ccfRNA), or an environmental DNA (eDNA) or an environmental RNA (eRNA).

29 Claims, 12 Drawing Sheets

| # of Copies | Mutant | RKO | Sigma |
|---|---|---|---|
| 100ng | 58823.52941 | 25.87 | |
| 10ng | 5882.352941 | 27.33 | 38.68 |
| 1ng | 588.2352941 | 30.95 | |
| 0.1ng | 58.82352941 | 34.93 | 38.71 |
| 0.01ng | 5.882352941 | 38.25 | |
| 0.001ng | 0.588235294 | 38.93 | |

Input Copy Number vs Detection Ct

Log(copies of input)

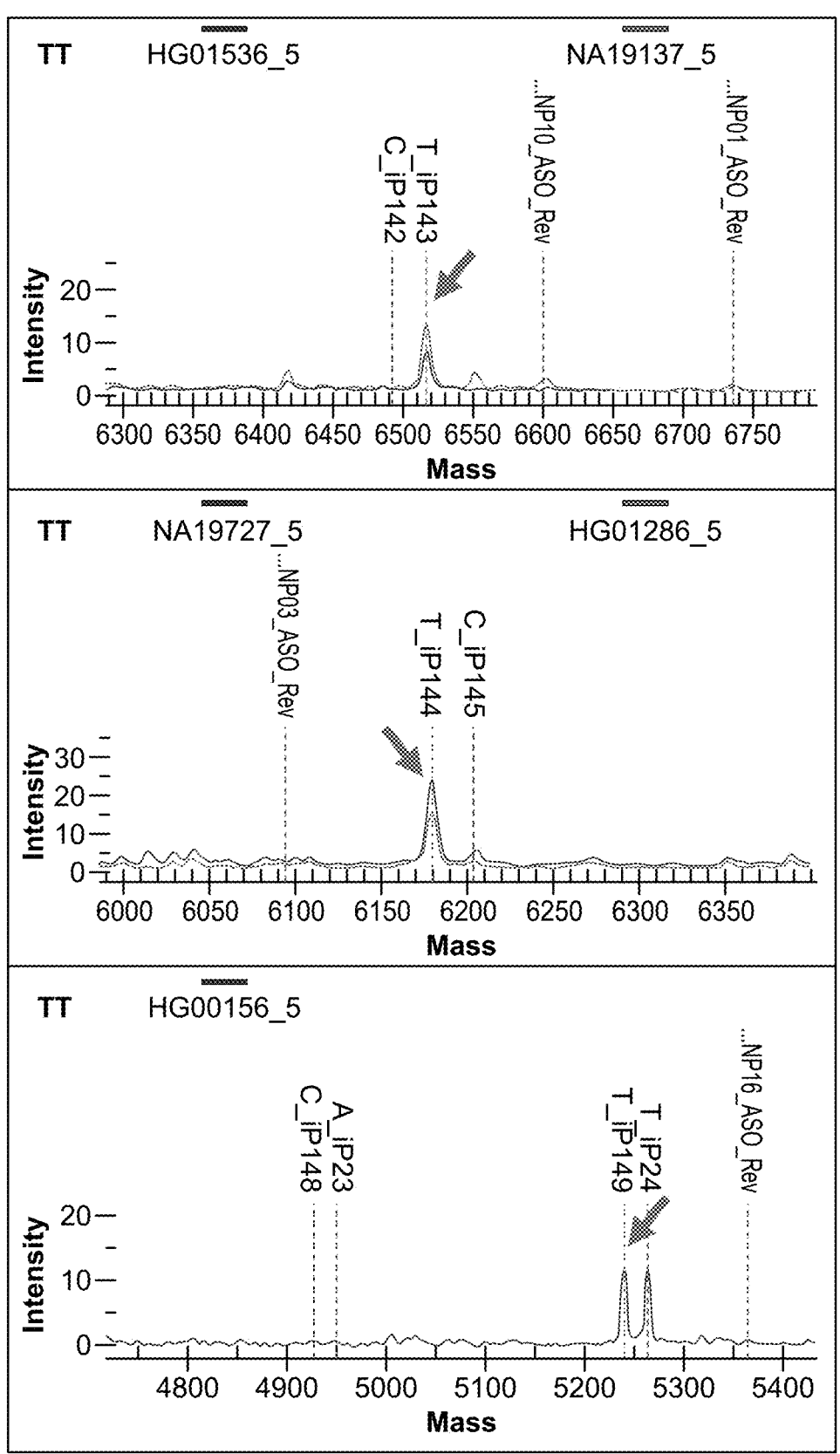
FIG. 10 (Cont.1)

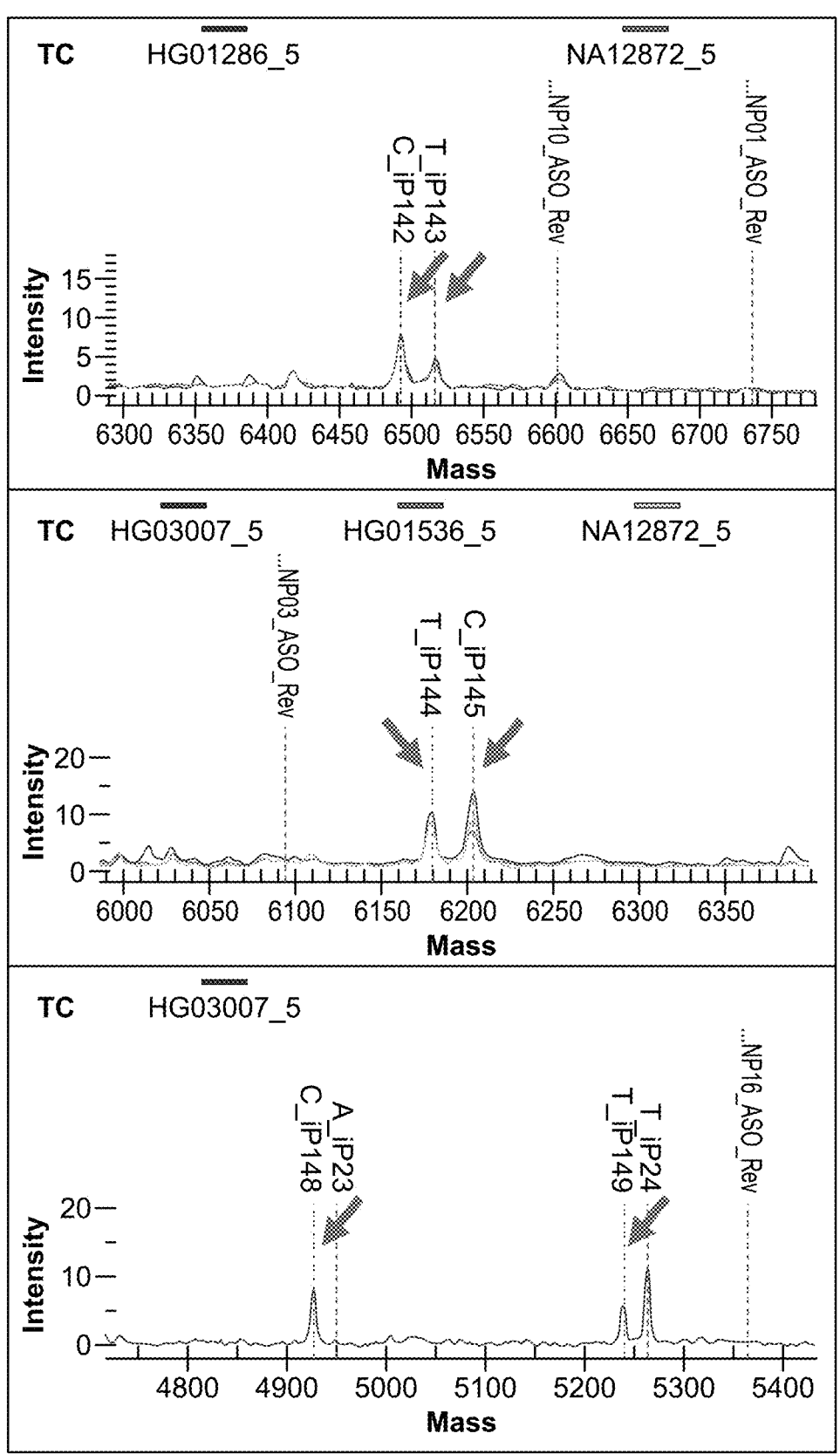
FIG. 10 (Cont.2)

METHODS FOR THE DETECTION OF A NUCLEIC ACID

RELATED APPLICATIONS

This U.S. National Phase Patent application claims benefit of priority under 35 U.S.C. § 371 to Patent Convention Treaty (PCT) International Application PCT/US2022/052371, filed Dec. 9, 2022, now pending, which claims the benefit of priority under 35 U.S.C. § 119(e) of U.S. Provisional Application Ser. No. 63/287,854, filed Dec. 9, 2021, now expired. The aforementioned applications are expressly incorporated herein by reference in their entirety and for all purposes. All publications, patents, patent applications cited herein are hereby expressly incorporated by reference for all purposes.

TECHNICAL FIELD

This invention generally relates to molecular biology and high-throughput analysis of nucleic acids from, for example, genomes or transcriptomes. In alternative embodiments, provided are polynucleotide-based methods of detecting the presence of a particular nucleic acid sequence including detection at single nucleotide resolution. Also included are primer-based nucleic acid amplification methods capable of detecting the presence of a particular nucleic acid sequence including detection at single nucleotide resolution. In alternative embodiments, the detection is performed in such a way that relative amounts, or absolute amounts of the detected nucleic acid sequence can be determined.

BACKGROUND

The detection of specific nucleic acids is important in the study of normal and abnormal biological states. Thus, with the advent of the liquid biopsy, detection of specific nucleic acids, particularly nucleic acids present in low amounts, including at the resolution of a single nucleotide, has become more important than ever.

Cell-free nucleic acids (cfNA) include circulating cell-free DNA (ccfDNA) and circulating cell-free RNA (ccfRNA) and are present in everyone's blood, with most derived from healthy, normal cells. However, in pregnant women, small amounts of fetal DNA are also present and can be used to look for genetic diseases in a procedure known as non-invasive prenatal testing (NIPT). Similarly, in solid organ transplants (SOT), minute amounts of donor-derived cell-free DNA (dd-cfDNA) can be used to detect acute rejection for a variety of organs. In cancer, scant levels of circulating tumor DNA (ctDNA) have been used to detect early recurrence of disease. Cell-free RNA has also been detected in various diseases, including cancer. Types of ccfRNA include messenger RNA (mRNA), microRNA (miRNA), and long non-coding RNA (lncRNA).

Detecting these nucleic acids can be difficult when they are at low concentrations as they often are in cell-free nucleic acids (cfNA) and because they occur as short fragments. Reporter assays have been used, for example, allele-specific PCR (AS-PCR) to selectively amplify the desired target (a specific allele or somatic mutation), but require sufficient sequence between the PCR primers for the binding of a reporter sequence. This increases the PCR assay "footprint", which with the short pieces of DNA and RNA typical in liquid biopsy samples lowers the detection rate. Nonlimiting examples of reporter assays include TAQMAN™ probes and molecular beacons.

Bulk mRNA released by organisms into their environment (eRNA) can be used to determine both the taxonomic composition and gene-expression profile of a complex community of macro-organisms. However, RNA in environmental media (eRNA) degrades rapidly and frequently cannot be detected in biologically meaningful quantities.

Sometimes the increased assay footprint that occurs when sufficient sequence between the PCR primers for the binding of a reporter sequence is acceptable, but differentiating between target nucleic acids that differ by a single nucleotide can be problematic due to small differences in the melting temperature ($T_M$, or primer melting temperature; Tm is by definition is the temperature at which one half of a DNA duplex will dissociate to become single-stranded and indicates duplex stability) between the reporter probes and the target sequences, for example when using TAQMAN™ reporters or molecular beacons that are intended to differentiate between targets that differ by only one nucleotide.

These reporter assays may be used in both qualitative assays and in quantitative assays, for example quantitative PCR (qPCR) and digital PCR (dPCR), including droplet digital PCR (ddPCR). Sometimes, a specific allele is not targeted, just a specific sequence, for example a specific transcript, but the interposition of a reporter target sequence still increases the PCR assay "footprint", which with the short pieces of fragmented target lowers the detection rate.

SUMMARY

In alternative embodiments, provided are methods for detecting a target nucleic acid sequence, comprising:

(a) providing or having provided a sample (optionally the sample comprises a biological sample) comprising a target nucleic acid, and optionally the biological sample comprises a biological material comprising the target nucleic acid, wherein optionally the target nucleic acid comprises a cell free nucleic acid (cfNA), optionally a cell-free DNA (cfDNA) or a cell-free RNA (cfRNA), or a circulating cell-free DNA (ccfDNA) or a circulating cell-free RNA (ccfRNA), or an environmental DNA (eDNA) or an environmental RNA (eRNA), optionally the target nucleic acid comprises a cell-derived nucleic acid or a viral-derived nucleic acid, and optionally the cell-derived nucleic acid can be intact or fragmented, or libraries derived from the nucleic acid sample;

(b) providing or having provided a first synthetic nucleic acid polynucleotide primer, wherein the first synthetic nucleic acid polynucleotide primer comprises:

(i) sufficient nucleotide residues to base pair (or selectively bind or anneal) to the target nucleic acid sequence under physiologic conditions, and (ii) one or more 5' nucleotide residues (5' to the sequence of (i)) that do not match (or are not complementary to) the target nucleic acid, and this non-matching sequence comprises and contains one or more *other* residues (or "R" residue or sequence as illustrated in FIG. 1) that when in double-stranded conformation can be specifically recognized and cleaved by an exonuclease or an endonuclease;

(c) providing or having provided a DNA polymerase, and an exonuclease or endonuclease capable of recognizing and cleaving the *other* residues (or "R" residue or sequence, as illustrates in FIG. 1) contained in the one or more non-target annealing 5' nucleotide residues of the first synthetic nucleic acid polynucleotide primer when the 5' nucleotide residues and the *other* residues (or "R") sequence are in double-stranded form, and the exonuclease or endonuclease are not capable of cleaving the 5' nucleotide residues or the *other* residues (or "R") sequence when the 5' nucleotide residues and the *other* residues (or "R") sequence are in single-stranded form;

(d) contacting the first synthetic nucleic acid polynucleotide to the sample under conditions wherein the synthetic nucleic acid polynucleotide is capable of annealing to the target nucleic acid;

(e) extending the length of the first synthetic nucleic acid polynucleotide primer in a 5' to 3' direction using the DNA polymerase using the target nucleic acid as a template, thereby generating an extended synthetic nucleic acid polynucleotide primer;

(f) providing or having provided a second (or return or a reverse) synthetic nucleic acid primer capable of binding or selectively annealing to the 3' end of the extended first synthetic nucleic acid polynucleotide primer (extended in step (e)), and binding or selectively annealing the second (or return or the reverse) synthetic nucleic acid to the extended synthetic nucleic acid polynucleotide primer;

(g) extending the length of the second (or return or the reverse) synthetic nucleic acid in a 5' to 3' direction using the DNA polymerase using the extended first synthetic nucleic acid polynucleotide primer as a template, and incorporating in the extended length complementary bases of the one or more 5' nucleotide residues that did not initially match (or was not complementary to) the target nucleic acid (including the *other* residues (or "R") sequence), thereby generating a double-stranded oligonucleotide comprising: the one or more 5' nucleotide residues of the first synthetic nucleic acid that did not initially match (or was or were not complementary to) the target nucleic acid; and, in annealed configuration, the corresponding complementary sequence; and (h) contacting the double-stranded oligonucleotide with the exonuclease or endonuclease, thereby cleaving the *other* residue (or "R") sequence that did not initially match (or was not complementary to) the target nucleic acid from the double-stranded oligonucleotide, thereby separating the one or more 5' nucleotide residues sequence and generating one or more fragments of single stranded nucleotide, wherein the generation or presence the one or more fragments of single-stranded nucleotide indicates the presence of the target nucleic acid, and optionally the one or more fragments of single-stranded nucleotide generated by this exemplary method are detected, and optionally qualified.

In alternative embodiments of methods as provided herein: the second synthetic nucleic acid may be similarly designed as the first synthetic acid so that under similar conditions single-stranded oligonucleotides reporter molecules are produced from the second synthetic nucleic acid.

In alternative embodiments of methods as provided herein:

the methods further comprise a step (i), comprising detecting presence of the one or more fragments of single-stranded nucleotide or oligonucleotide, or detecting the single-stranded residue having the *other* residue (or "R") sequence, to detect or indicate the presence of the target nucleic acid (or, thereby resulting in the detection of the target nucleic acid by inference to the presence of the detected single-stranded residue or oligonucleotide, optionally having the *other* residue (or "R") sequence);

the one or more 5' nucleotide residues that do not match (or are not complementary to) the target nucleic acid on the first synthetic nucleic acid polynucleotide primer (or the *other* residue (or "R") sequence as in FIG. 1) comprise or comprises at least one ribonucleotide;

the endonuclease is a non-sequence-specific endonuclease or an endonuclease that specifically cleaves an RNA:DNA hybrid oligonucleotide;

the non-sequence-specific endonuclease is or comprises the activity of a ribonuclease H or ribonuclease H2;

the one or more 5' nucleotide residues that do not match (or are not complementary to) the target nucleic acid on the first synthetic nucleic acid polynucleotide primer (or the *other* residue (or "R") sequence as in FIG. 1) comprise or comprises a damaged or modified nucleotide, and the endonuclease or the exonuclease removes the damaged or modified nucleotide;

the one or more 5' nucleotide residues that do not match (or are not complementary to) the target nucleic acid on the first synthetic nucleic acid polynucleotide primer (or the *other* residue (or "R") sequence as in FIG. 1) comprise or comprises a thymine glycol and the endonuclease is endonuclease VIII;

the first synthetic nucleic acid polynucleotide primer is annealed to the target nucleic acid, and after amplification and generation of a double-stranded nucleic acid, the one or more or the 5' nucleotide residues that do not match (or are not complementary to) the target nucleic acid (or the *other* residue (or "R") sequence as in FIG. 1) are cleaved by an endonuclease or exonuclease activity such that: both 5' and 3' fragments of the synthetic nucleic acid polynucleotide primer are produced, or, both 5' and 3' fragments of the synthetic nucleic acid polynucleotide primer are produced and one or more internal fragments of the synthetic nucleic acid polynucleotide primer are produced, see FIG. 7B;

the extended first synthetic nucleic acid polynucleotide primer acts as a template in the amplification of a second (or return or a reverse synthetic nucleic acid primer), and as a consequence of the amplification (generating a double-stranded nucleic acid) the one or more unpaired residues of the one or more or the 5' nucleotide residues that do not match (or are not complementary to) the target nucleic acid, or the *other* residue (or "R") sequence as in FIG. 1, are cleaved by an enzyme activity such that: 5' and 3' fragments are produced; and 5' and 3' fragments and one or more internal fragments are produced;

the one or more cleavage fragments are detected by virtue of their: mass, composition, length, sequence and/or fluorescence or bioluminescent or equivalent;

the amplification produces or generates one or more nucleic acid fragments that are proportional to the number of target nucleic acid polynucleotides present in the sample, wherein optionally the method comprises two, three, four or five or more, or between about one and 100 rounds, or between about 2 and 60, or between about 5 and 50, of amplification);

the synthetic nucleic acid polynucleotide primer is or comprises an allele-specific primer;

the amplification of only one allele is suppressed;

the target nucleic acid is or comprises a complementary DNA created from an RNA template, where optionally the RNA template is or is derived from a cell-free RNA (cfRNA), or a circulating cell-free RNA (ccfRNA), or an environmental RNA (eRNA);

an annealed synthetic nucleic acid polynucleotide primer is first extended by one or more nucleotides before a ribonucleic acid residue in the annealed synthetic nucleic acid polynucleotide primer can be cleaved by an endonuclease or an exonuclease;

the annealing and extension of the synthetic nucleic acid polynucleotide primer occurs at a temperature wherein if enzymatic cleavage at the ribonucleic acid residue occurs, displacement of resulting fragments by an uncleaved and unextended target nucleic acid poly- nucleotide is thermodynamically favored;

the one or more 5' nucleotide residues that do not match (or are not complementary to) the target nucleic acid comprise (or have covalently conjugated thereto) a fluorescent or bioluminescent or equivalent or equiva- lent moiety (F);

the one or more 5' nucleotide residues that do not match (or are not complementary to) the target nucleic acid comprise (or have covalently conjugated thereto) a quencher molecule (Q), wherein the quencher molecule is capable of quenching or substantially lowering or dampening the signal of the fluorescent or biolumines- cent moiety or equivalent (F) when the quencher mol- ecule (Q) is in proximity, or within 1 to about 20, or within 2 to about 40, or 3 to about 50 or 4 to about 60, or more, nucleotide residues, of the fluorescent or bioluminescent moiety, or equivalent (F), and the one or more 5' nucleotide residues between the quencher molecule (Q) and the fluorescent or bioluminescent moiety or equivalent (F) comprise a sequence (for example, the *other* residue (or "R") sequence as in FIG. 1 and FIG. 2) recognized by an endonuclease or an exonuclease and cleaved when recognized by the endonuclease or the exonuclease when in double- stranded form; and/or the quencher molecule (Q) molecule is positioned 5' or 3' to the fluorescent or bioluminescent moiety, or equiva- lent (F), in the one or more 5' nucleotide residues that do not match (or are not complementary to) the target nucleic acid (see FIG. 2).

In alternative embodiments, provided are methods for detecting a target nucleic acid sequence (see for example, FIG. 5 and FIG. 6), comprising:

(a) providing or having provided a sample (optionally a biological sample) comprising a target nucleic acid (optionally the target nucleic acid comprises a biologi- cal material comprising the target nucleic acid), wherein optionally the target nucleic acid comprises a cell free nucleic acid (cfNA), optionally a cell-free DNA (cfDNA) or a cell-free RNA (cfRNA), or a circulating cell-free DNA (ccfDNA) or a circulating cell-free RNA (ccfRNA), or an environmental DNA (eDNA) or an environmental RNA (eRNA);

(b) providing or having provided a first synthetic nucleic acid polynucleotide primer, wherein the first synthetic nucleic acid polynucleotide primer comprises:

(i) sufficient nucleotide residues to base pair (or selec- tively bind or anneal) to the target nucleic acid sequence under physiologic conditions; and (ii) one or more 3' nucleotide residues that because of the proximity to the 3' end of the synthetic nucleic acid polynucleotide primer are not cleaved by an enzyme, wherein optionally the enzyme is an endonuclease or an endonuclease;

(c) providing or having provided a DNA polymerase, and an exonuclease or endonuclease capable of recognizing one or more 3' nucleotide residues of the synthetic nucleic acid polynucleotide primer and cleaving a double-stranded form of the one or more 3' nucleotide residue oligonucleotide, and based on the recognizing the exonuclease or endonuclease cleaves the double- stranded one or more 3' nucleotide residue oligonucle- otide;

(d) contacting the first synthetic nucleic acid polynucle- otide to the sample under conditions wherein the first synthetic nucleic acid polynucleotide is capable of annealing to, and anneals to, the target nucleic acid;

(e) extending the length of the first synthetic nucleic acid polynucleotide primer in a 5' to 3' direction using the DNA polymerase using the target nucleic acid as a template, thereby generating an extended first synthetic nucleic acid polynucleotide primer and a double- stranded oligonucleotide, wherein optionally the first synthetic nucleic acid poly- nucleotide primer is not extended the full 3' length of the target nucleic acid, and optionally the first synthetic nucleic acid polynucle- otide primer is extended one to 10, or two to about 20, or about 3 to about 30, or about 4 to about 40, or more, nucleotide residues by the polymerase;

(f) contacting the double-stranded oligonucleotide with the exonuclease or endonuclease, thereby cleaving the sequence (optionally the *other* residue (or "R") sequence) on the extended first synthetic nucleic acid polynucleotide primer that was not initially recognized or cleavable by the endonuclease or exonuclease, thereby generating one or more fragments of single- stranded nucleotide, wherein the generation or presence the one or more fragments of single-stranded nucleotide indicates the presence of the target nucleic acid, and optionally the one or more fragments of nucleotide generated by this exemplary method are detected, and optionally qualified.

In alternative embodiments, provided are methods for detecting a target nucleic acid sequence, comprising:

(a) providing or having provided a sample (wherein optionally the sample comprises a biological sample) comprising a target nucleic acid (optionally the target nucleic acid comprises a biological material compris- ing a target nucleic acid, wherein optionally the target nucleic acid comprises a cell free nucleic acid (cfNA), optionally a cell-free DNA (cfDNA) or a cell-free RNA (cfRNA), or a circulating cell-free DNA (ccfDNA) or a circulating cell-free RNA (ccfRNA), or an environ- mental DNA (eDNA) or an environmental RNA (eRNA));

(b) providing or having provided a first synthetic nucleic acid polynucleotide primer, wherein the first synthetic nucleic acid polynucleotide primer comprises:

(i) sufficient nucleotide residues to base pair (or selec- tively bind or anneal) to the target nucleic acid sequence under physiologic conditions, and (ii) one or more 3' nucleotide residues (optionally the *other* residue (or "R") sequence) that because of the proximity to the 3' end of the synthetic nucleic acid polynucleotide primer are not cleaved by an enzyme, optionally the enzyme is an endonuclease or an endonuclease;

(c) providing or having provided a DNA polymerase, and an exonuclease or endonuclease capable of recognizing one or more 3' nucleotide residues of the synthetic nucleic acid polynucleotide primer (optionally the *other* residue (or "R") sequence) in the form of an extended double-stranded oligonucleotide, and based on the recognizing the exonuclease or endonuclease is capable of cleaving the double-stranded oligonucleotide;

(d) contacting the first synthetic nucleic acid polynucleotide to the sample under conditions wherein the first synthetic nucleic acid polynucleotide is capable of annealing to the target nucleic acid;

(e) extending the length of the first synthetic nucleic acid polynucleotide primer in a 5' to 3' direction using the DNA polymerase using the target nucleic acid as a template, thereby generating an extended synthetic nucleic acid polynucleotide primer and a double-stranded oligonucleotide, wherein optionally the synthetic nucleic acid polynucleotide primer is not extended the full 3' length of the target nucleic acid, and optionally the synthetic nucleic acid polynucleotide primer is extended one to about 10, or two to about 20, or about 3 to about 30, or about 4 to about 40, or more, nucleotide residues by the polymerase;

(f) contacting the double stranded oligonucleotide with the exonuclease or endonuclease, thereby cleaving the sequence of the extended synthetic nucleic acid polynucleotide primer that was not initially recognized or cleavable by the endonuclease or exonuclease at the *other* residue (or "R") sequence), thereby generating one or more fragments of single-stranded nucleotide, wherein the annealing and extension (extending) reaction conditions comprise a temperature where the cleaved (shortened) extended synthetic nucleic acid polynucleotide primer is displaced from the target nucleic acid by an unextended (uncleaved) synthetic nucleic acid polynucleotide primer, in other words, the annealing and extension occurs at a temperature that thermodynamically favors binding of the uncleaved and unextended nucleic acid primer over the cleaved and extended primer, and the newly annealed uncleaved and unextended nucleic acid primer is extended in a 5' to 3' direction using the DNA polymerase using the target nucleic acid as a template, and again this extended nucleic acid primer can now be cleaved by the enzyme, thus generating additional cleaved primer fragments (both 5' and 3' fragments), wherein the generation or presence the one or more 5' and/or 3' fragments of single-stranded nucleotide indicates the presence of the target nucleic acid, and optionally the method comprises detecting (and optionally also quantifying) the one or more 5' and/or 3' fragments. In alternative embodiments, oligonucleotides, or 5' and/or 3' fragments of single-stranded nucleotide, as generated by methods as provided herein, are detected and/or quantified using any method, for example, MALDI-TOF MS (matrix assisted laser desorption ionization-time of flight mass spectrometry (MALDI-TOF MS)).

In alternative embodiments, provided are kits or products of manufacture comprising materials, optionally enzymes (for example, endonucleases, exonucleases, DNA polymerases, or a thermostable RNase H2 enzyme (TS RNase H2)) and/or synthetic DNA polynucleotides, for practicing a method as provided or described herein, and optionally further comprising instructions for practicing a method as provided or described herein.

In alternative embodiments, provided are kits comprising materials for practicing methods as provided herein, and optionally also comprising instructions for practicing methods as provided herein.

The details of one or more exemplary embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference in their entireties for all purposes.

DESCRIPTION OF DRAWINGS

The drawings set forth herein are illustrative of exemplary embodiments provided herein and are not meant to limit the scope of the invention as encompassed by the claims.

In all cases the *other* residue may refer to one or more residues. Nonlimiting examples of *other* residues denoted by the "R" symbol in the figures are listed in Table 1 along with their corresponding cleavage enzymes:

TABLE 1

| *other* nucleotide | Enzyme |
| --- | --- |
| Four or more RNA residues | RNase H1 |
| One or more RNA residues | RNase H2 |
| Damaged pyrimidines (e.g., Thymine Glycol) | Endonuclease VIII |
| Apurinic/Apyrimidinic sites | Endonuclease IV, Tth Endonuclease IV, T4 pyrimidine DNA glycosylase |
| 5mC | ROS1, DEMETER, DML2, DML3 |
| 5hmC | ROS1, DEMETER, DML2, DML3 |

Figure 1:
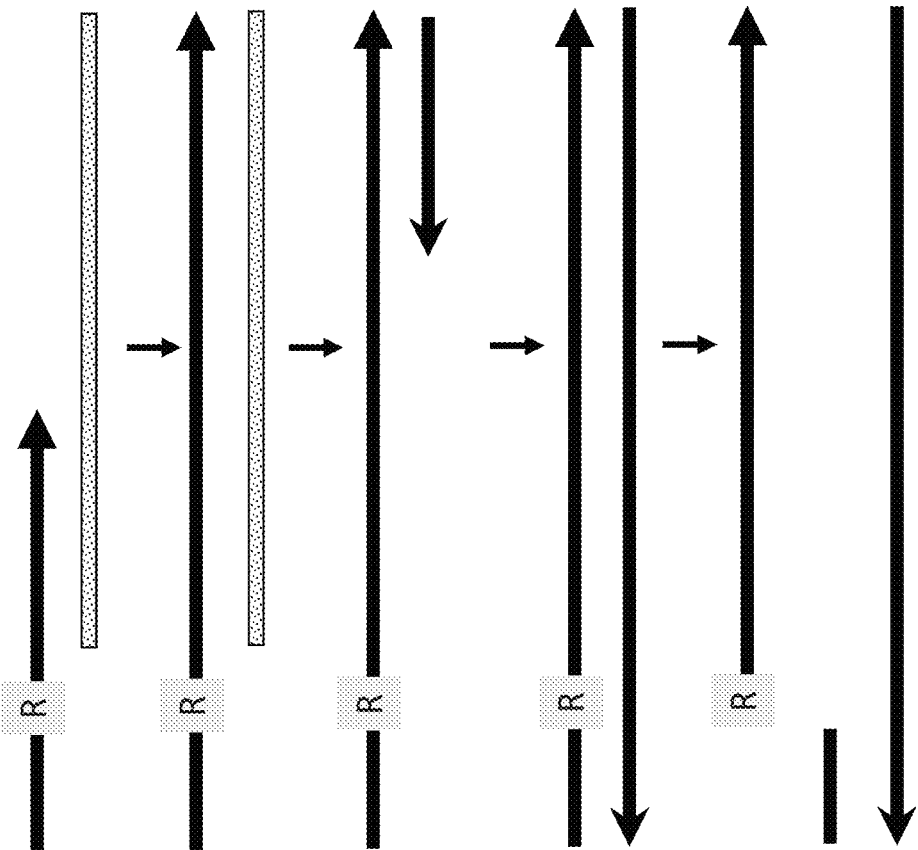

FIG. 1 schematically illustrates an exemplary method as provided herein, comprising use of a first nucleic acid polynucleotide amplification primer where the 3' proximal sequence matches and is annealed to a target sequence and the 5' proximal sequence of the polynucleotide amplification primer does not match the target sequence and contains one or more *other* residues (or "R" residue or sequence as illustrated in this figure). The first primer (the polynucleotide amplification primer) is extended by a polymerase, for example, a DNA polymerase. Subsequently, a return primer binds (or anneals) to the extended first primer and is extended by a polymerase that copies over the *other* residue (or "R" residue or sequence) on the polynucleotide amplification primer. Now in a double-stranded configuration, the *other* residue (or "R" residue or sequence) is cleaved (in this example, on the 5' side, though it could also be cleaved on the 3' side, or removed). The presence of either resulting fragment or both indicates the presence of the target sequence.

Figure 2:
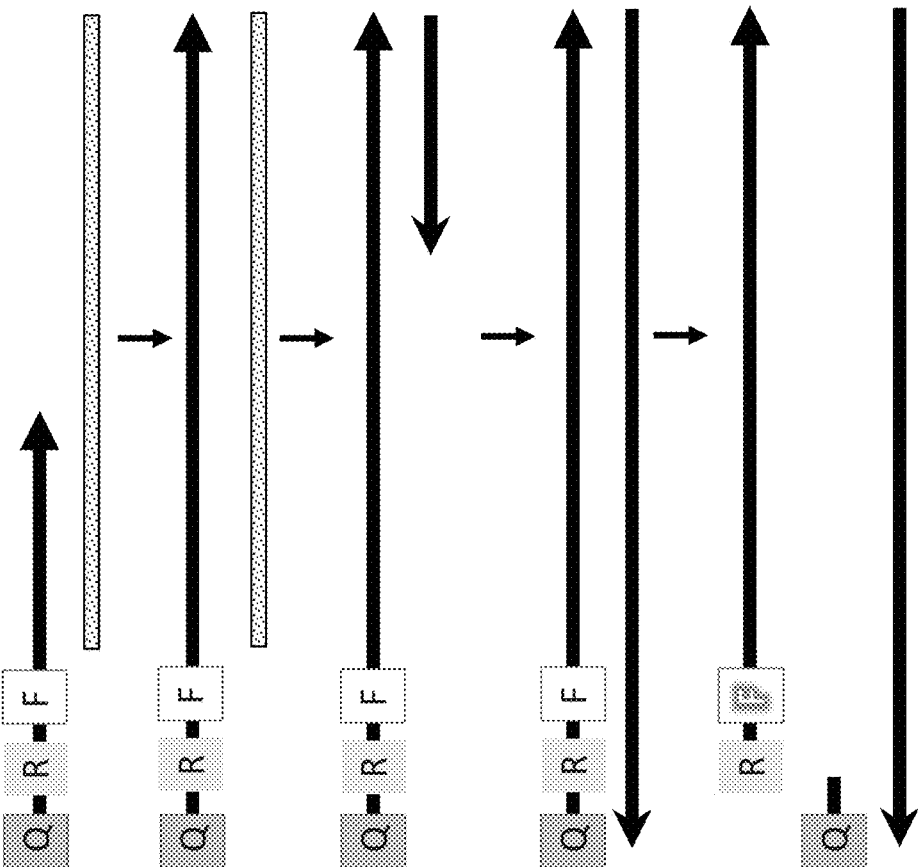

FIG. 2 schematically illustrates an exemplary method as provided herein, comprising use of a first nucleic acid polynucleotide amplification primer where the 3' proximal sequence matches and is annealed (or base paired) to a target sequence and the 5' proximal sequence does not match the target sequence and contains one or more *other* residues (or "R" residue or sequence, as indicated in this figure) flanked by a fluorescence or bioluminescent or equivalent quencher (Q), in this example on the 5' side of the *other*, or R, residue and a fluorescent or bioluminescent or equivalent moiety (F) or equivalent, in this example on the 3' side of the *other*, or R, residue (however, in alternative embodiments, the fluorescence or bioluminescent or equivalent quencher (Q) is on the 3' side of the *other*, or R, residue and the fluorescent or bioluminescent or equivalent moiety (F) or equivalent is on the 5' side of the *other*, or R, residue). The quencher and fluorescent or bioluminescent or equivalent moieties are sufficiently linked, or in sufficient proximity, to each other such that the quencher moiety is able to quench the fluorescence or bioluminescent or equivalent moiety. The first primer is extended by a polymerase. Subsequently, the return primer binds to the extended first primer and is extended by a polymerase that copies over the *other*, or R, residue. Now in a double-stranded configuration, the *other*, or R, residue is cleaved by the nuclease enzyme (for example, an endonuclease) (in this example, on the 5' side, though it could also be cleaved on the 3' side or removed). The quencher and fluorescent or bioluminescent or equivalent moieties are no longer linked (or in close proximity) to each other and the fluorescence is enhanced. Detection of fluorescence or bioluminescence or equivalent indicates the presence of the target sequence.

Figure 3:
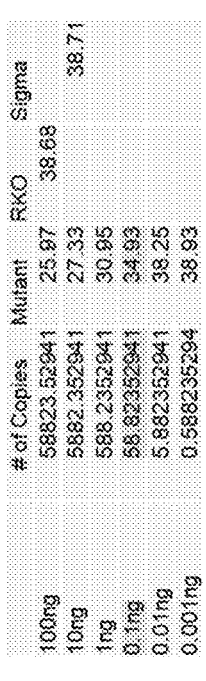
Figure 3:
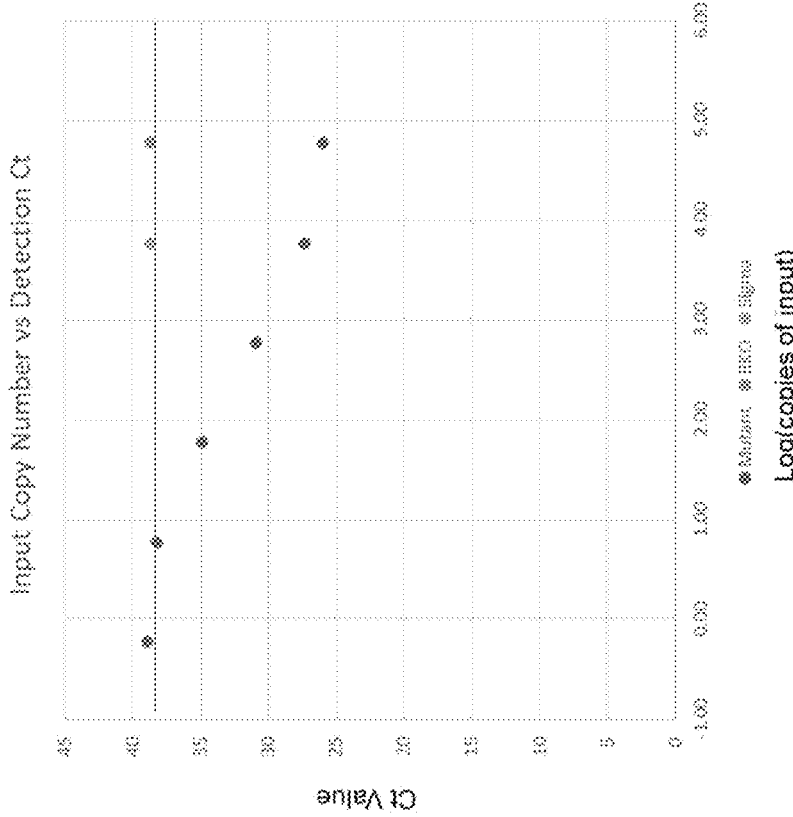

FIG. 3 graphically illustrates qPCR results using an allele-specific primer for the detection of a KRAS (Kirsten rat sarcoma virus) c.38G>T mutation using the exemplary method depicted in FIG. 2. Results demonstrate that the mutant can be easily distinguished from the wild type when as few as 59 mutant copies are present. RKO and Sigma DNAs are both wild type for the mutant.

Figure 4:
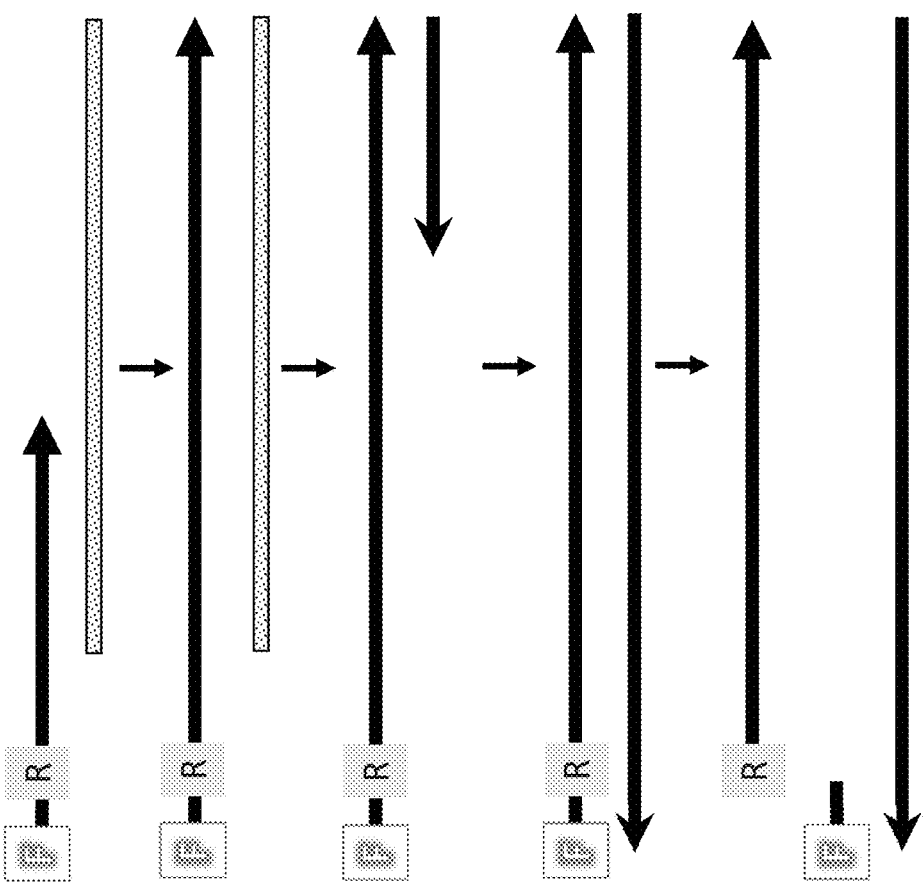

FIG. 4 schematically illustrates an exemplary method as provided herein, comprising use of a first nucleic acid polynucleotide amplification primer where the 3' proximal sequence (of the amplification primer) matches and is annealed (or is sufficiently complementary to anneal) to the target sequence, and the 5' proximal sequence (of the amplification primer) does not match the target sequence and contains one or more *other* residues (or "R") flanked by a fluorescent moiety or bioluminescent or equivalent or equivalent (F) on the 5' side of the *other* (or "R") residue. The first amplification primer is extended by a polymerase. Subsequently, a second, or return, amplification primer binds (or anneals) to the extended first amplification primer, and is extended by a polymerase that copies over the 5' end of the first amplification primer, including the *other* (or "R") residue. Now in a double-stranded configuration, the *other* (or "R") residue is cleaved (in this example, on the 5' side, though it could also be cleaved on the 3' side or removed) by the enzyme. The fluorescent or bioluminescent or equivalent moiety (F) is now linked to a much smaller molecule than the original first primer. The fluorescence or bioluminescent or equivalent polarization signal of the smaller molecule (the cleaved residue) decays faster than that of the original first amplification primer, indicating the presence of the target sequence.

Figure 5:
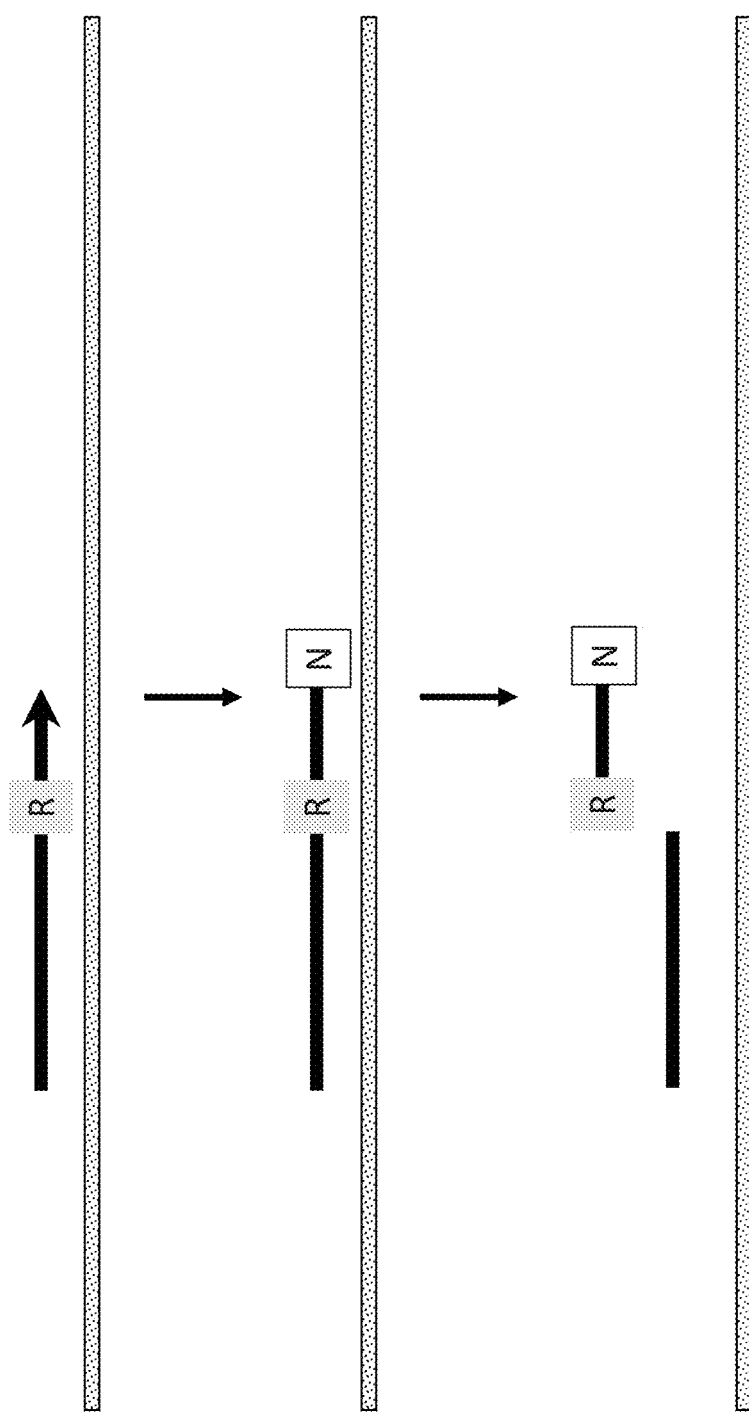

FIG. 5 schematically illustrates an exemplary method as provided herein, comprising use of a first nucleic acid polynucleotide (or first amplification primer) annealed to a target sequence. The first nucleic acid polynucleotide contains one or more *other* (or "R") residues that because of their proximity to the 3' end are not cleaved by an enzyme (for example, not cleavable by an endonuclease or exonuclease). When the first nucleic acid polynucleotide is extended (for example, enzymatically extended) by one or more nucleotides (depicted as "N" in the figure) the *other* (or "R") residues are recognized by an enzyme and cleaved (in this example, on the 5' side, though with alternate enzymes cleavage could take place on the 3' side or the residue could be removed). The presence of resulting fragments, for example, 5' fragments or 3' fragments, or both, indicates the presence of the target sequence.

Figure 6:
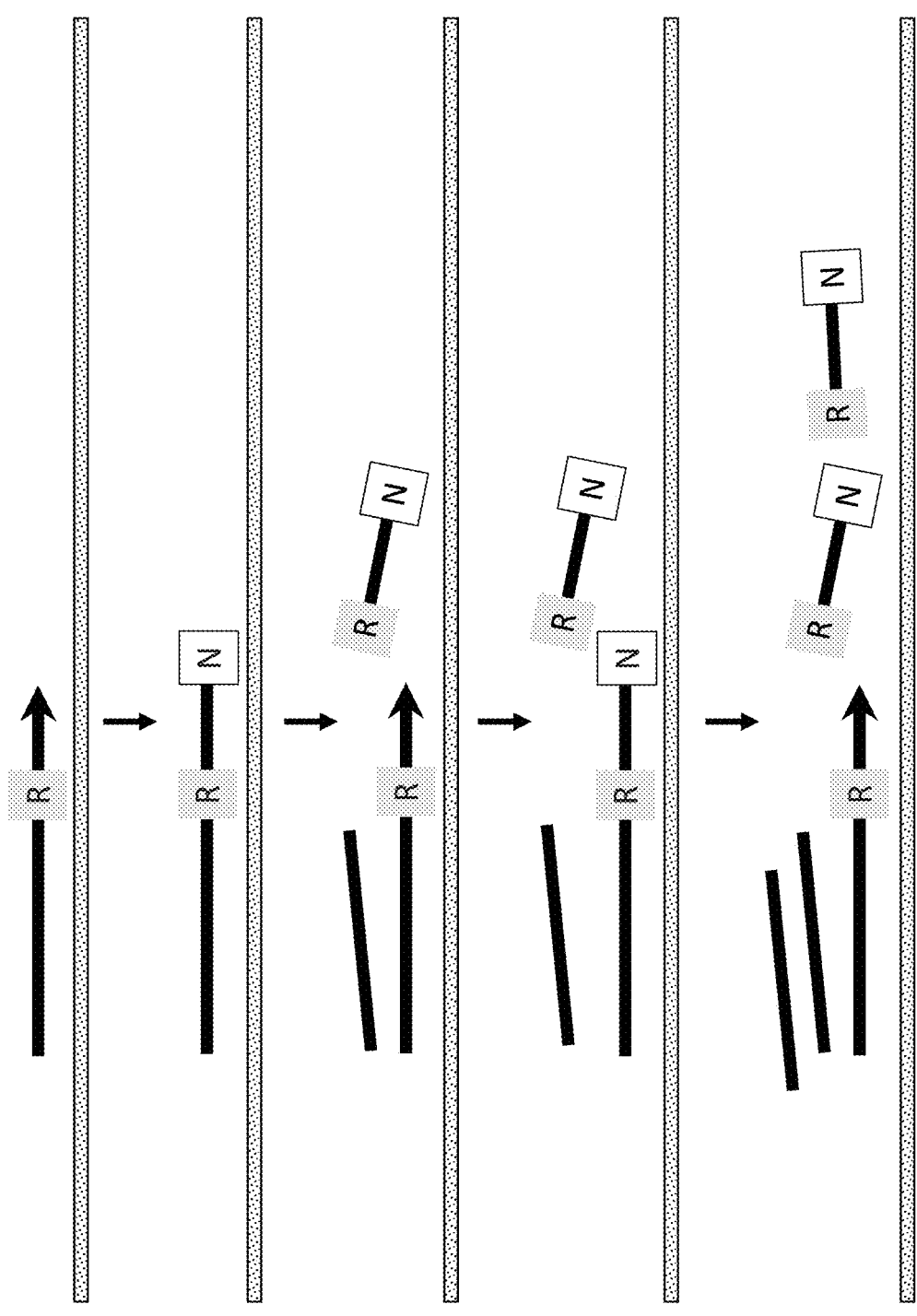

FIG. 6 schematically illustrates an exemplary method as provided herein, comprising use of a first nucleic acid polynucleotide (or first amplification primer) annealed to a target sequence. The first nucleic acid polynucleotide contains one or more *other* (or "R") residues that because of the proximity to the 3' end are not cleaved by an enzyme. When the first nucleic acid polynucleotide is extended (for example, enzymatically extended) by one or more nucleotides the *other* (or "R") residues are recognized by an enzyme and cleaved (in this example, on the 5' side, though with alternate enzymes cleavage could take place on the 3' side or the residue could be removed). The annealing and extension of the first nucleic acid polynucleotide occurs at a temperature where if the cleavage at the *other* (or "R") or ribonucleic acid residue occurs, then the resulting fragments are displaced by an uncleaved and unextended first nucleic acid polynucleotide (or first amplification primer), in other words, the annealing and extension occurs at a temperature that thermodynamically favors binding of the uncleaved and unextended first amplification primer over the cleaved and extended primer. The displacing first nucleic acid polynucleotide is in turn extended and cleaved; and as this process continues, cleaved fragments accumulate. The presence of resulting fragments, for example, accumulation of 5' fragments or 3' fragments, or both, indicates the presence of the target sequence.

Figure 7B:
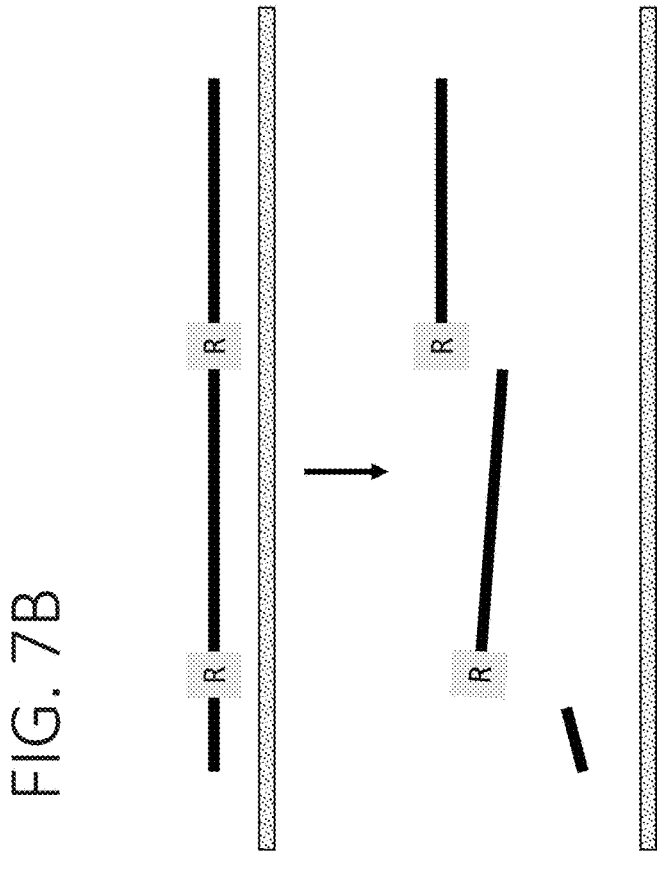
Figure 7A:
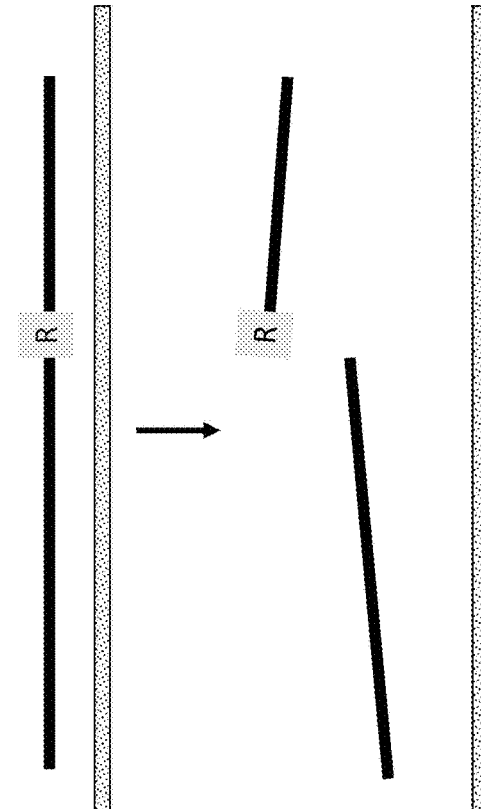

FIG. 7A-B schematically illustrate an exemplary method as provided herein for the detection by a first nucleic acid polynucleotide (or first amplification primer) of a second nucleic acid polynucleotide (the target sequence). FIG. 4A illustrates a first amplification primer with only a single *other* (or "R") residue; FIG. 4B illustrates a first amplification primer with two *other* (or "R") residues; and in alternative embodiments, the first amplification primer contains multiple (for example, between about 2 and 10) *other* (or "R") residues.

FIG. 7A illustrates an exemplary method wherein a first nucleic acid polynucleotide with a single *other* (or "R") residue annealed to the target sequence. When annealed in a double-stranded configuration, the *other* (or "R") residue is enzymatically cleaved (in this example, on the 5' side, though it could also be cleaved on the 3' side or removed). The presence of either resulting fragment, for example, a 5' fragment and/or a 3' fragment, indicates the presence of the target sequence. In alternative embodiments, both fragments are detected.

FIG. 7B illustrates an exemplary method wherein a first nucleic acid polynucleotide with two *other* (or "R") residues are annealed to the target sequence. When annealed in a double-stranded configuration, the *other* (or "R") residues are enzymatically cleaved (in this example, on the 5' sides, though they could also be cleaved on the 3' sides or removed). The presence of any of the resulting fragments, i.e., the 5' fragment or the 3' fragment and/or the internal fragment, indicates the presence of the target sequence. In alternative embodiments, two or three fragments are detected. In alternative embodiments, as a control, one or more of the *other* (or "R") residues is/are annealed to an invariant nucleotide and the cleavage at that *other* (or "R") residue indicates that the target sequence is present; in addition, one or more *other* (or "R") residues can be annealed to a variant nucleotide and enzymatic cleavage can only take place if the *other* (or "R") nucleotide is base-paired to the variant nucleotide. The presence of resulting fragments, for example, a 5' fragment, a 3' fragment, an internal fragment or any combination of fragments indicates the presence of the target sequence.

Figure 8:
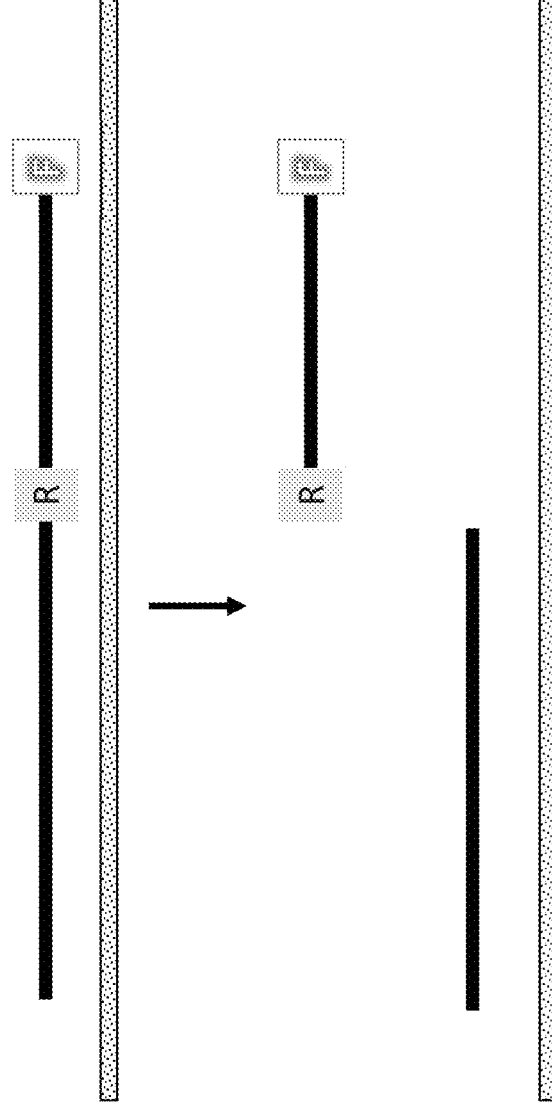

FIG. 8 schematically illustrates an exemplary method as provided herein, comprising use of a first nucleic acid polynucleotide with a single *other* (or "R") residue with a fluorescent or bioluminescent or equivalent moiety (for example, a fluor) attached to the 3' end, annealed to the target sequence. When annealed in a double-stranded configuration, the *other* (or "R") residue is cleaved (in this example, on the 5' side, though it could also be cleaved on the 3' side or removed). The fluorescent or bioluminescent or equivalent moiety is now linked to a much smaller molecule than the original, intact first nucleic acid polynucleotide. The fluorescence or bioluminescent or equivalent polarization signal of the smaller molecule decays faster than that of the original first primer, indicating the presence of the target sequence. The fluor could also be attached to the 5' end or attached internally.

Figure 9:
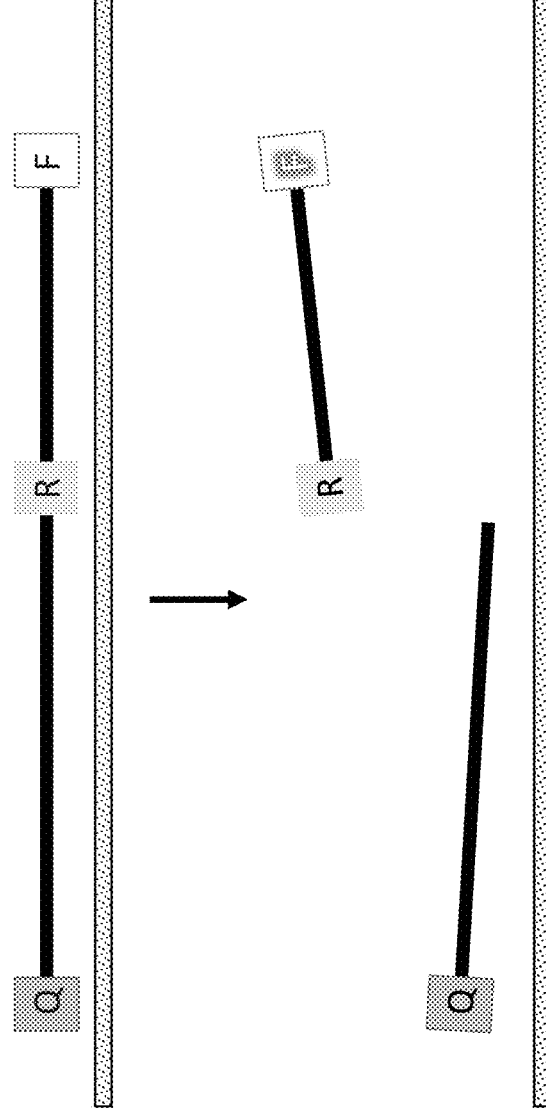

FIG. 9 illustrates a first nucleic acid polynucleotide annealed to a target sequence. The first nucleic acid polynucleotide contains one or more *other* (or "R") residues flanked by a fluorescence or bioluminescent or equivalent quencher (Q), in this example on the 5' side of the *other* (or "R") residue and a fluorescent or bioluminescent or equivalent moiety (F), in this example on the 3' side of the *other* (or "R") residue. When annealed in a double-stranded configuration, the *other* (or "R") residue is enzymatically cleaved (in this example, on the 5' side, though it could also be enzymatically cleaved on the 3' side or removed). The quencher (Q) and fluorescent or bioluminescent or equivalent moieties (F) are no longer linked to each other (or no longer are in sufficient spacially proximity to each other such that Q quenches the F signal) and the fluorescence or bioluminesce or equivalent is enhanced (in other words, the quencher (Q) is no longer close enough to the fluor, or fluorescent or bioluminescent or equivalent moiety or moieties (F), to dampen or quench the signal of the fluor, or fluorescent or bioluminescent or equivalent moiety) (F). Detection of fluorescence or bioluminescent or equivalent indicates the presence of the target sequence.

Figure 10:
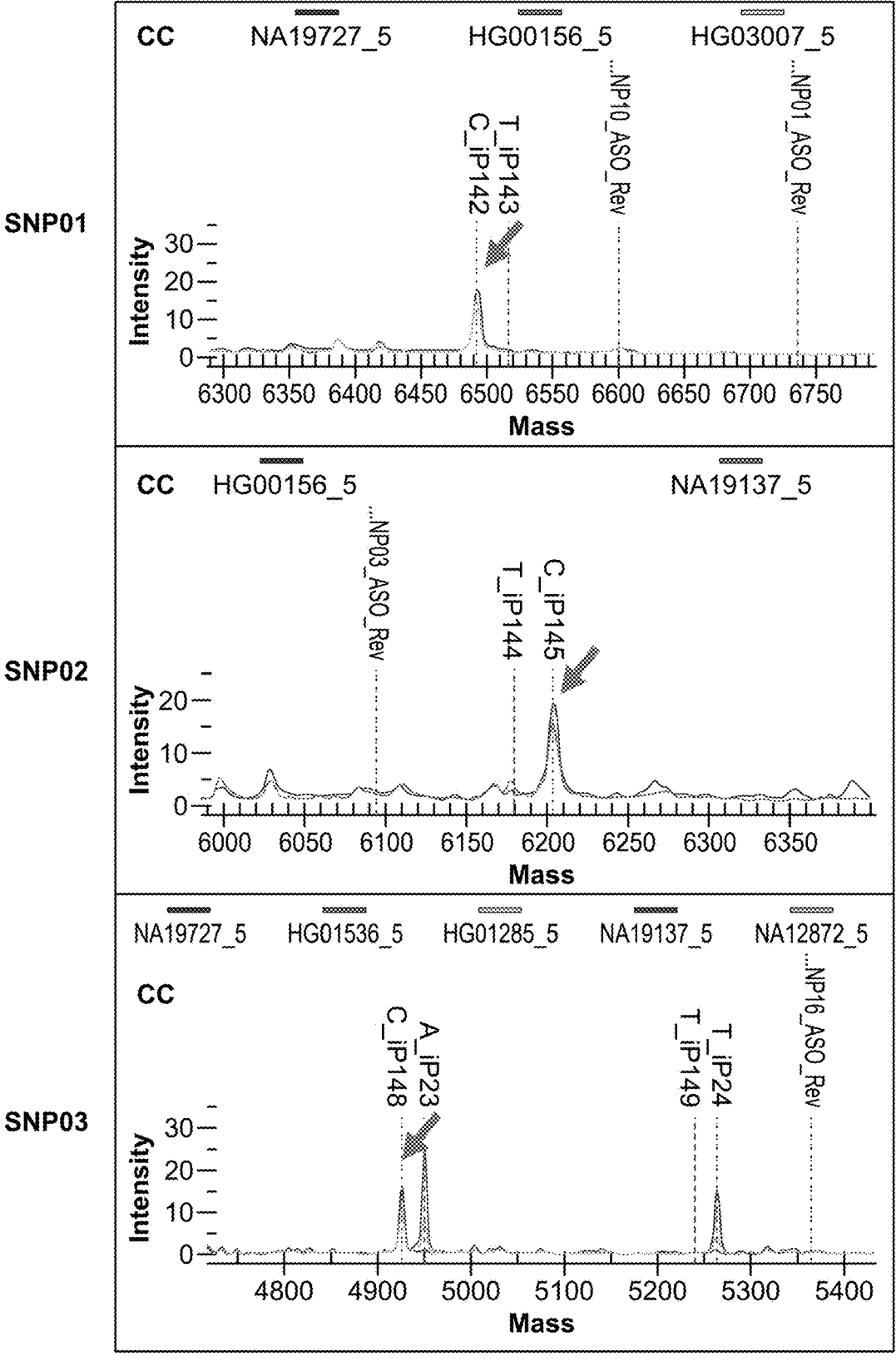

FIG. 10 illustrates data generated by MALDI-TOF MS (matrix assisted laser desorption ionization-time of flight mass spectrometry (MALDI-TOF MS)) detection of nucleic acid generated using an exemplary method as provided herein, as described in detail in Example 11, below.

Like reference symbols in the various drawings indicate like elements.

DETAILED DESCRIPTION

In alternative embodiments, provided are nucleic acid detection methods which can detect the presence of a specific sequence. In alternative embodiments, provided are polynucleotide-based nucleic acid compositions useful in methods that identify specific nucleic acid target sequences without the need for allowing sufficient interposing target sequence to support the binding of a reporter (for example as is the case with provided by the RNA residues. Analysis of the fragments by mass or length TAQMAN™ probes or molecular beacons). In alternative embodiments, provided are methods that use polynucleotide-based nucleic acid compositions to identify specific nucleic acid target sequences without the need for allowing sufficient interposing target sequence to support the binding of a reporter. In some embodiments, alternative allele(s) or mutation(s) present in a nucleic acid (or polynucleotide, or deoxyribonucleic acid (DNA) or ribonucleic acid (RNA)) sequence that differ from another sequence by as little as one nucleotide, are selectively amplified and detected in a manner allowing for analysis and measurement of the alternative allele(s) or mutation(s).

In alternative embodiments, provided are polynucleotide-based nucleic acid compositions useful in methods that identify alternative allele(s) or mutation(s) present in a nucleic acid (or polynucleotide, or deoxyribonucleic acid (DNA) or ribonucleic acid (RNA)) sequence that differ from another sequence by as little as one nucleotide, where the detection relies on the processing of a reporter that differentiates between the target sequences, similar to a TAQMAN™ probe or molecular beacon, but where there is a much reduced reliance on differential binding of the reporter to the targets and an extra level of stringency provided by the processing of the reporter.

In alternative embodiments, the target is detected by sequencing, hybridization, mass spectrometry, fluorescence or bioluminescent or equivalent or any other technology that can detect nucleic acid sequences, including those with nucleotide resolution.

In alternative embodiments, provided are synthetic DNA polynucleotides containing one or more RNA residues that are used in target-specific amplification that results in a signal being generated when the targeted sequence is present.

In alternative embodiments the synthetic DNA polynucleotide is an amplification primer containing one or more *other* (or "R") residues. The 3' end of the DNA polynucleotide is a gene-specific primer involved in amplification of a target sequence and the one or more *other* (or "R") residues are located at the 5' end of the DNA polynucleotide and are not complementary to the target sequence. When the 3' gene-specific moiety binds its target and in the presence of a DNA polymerase is extended to form a first-strand DNA and a return gene-specific primer binds to the first-strand DNA and is extended to form a double-stranded product, the one or more *other* (or "R") residues that are now base-paired are substrates for enzymatic digestion that cleaves the phosphodiester backbone at either the 5' side or 3' side of the one or more *other* (or "R") residues. The 5' end of the primer becomes detached from the rest of the primer, indicating the presence of the target sequence.

The presence of the detached 5' end of the primer or of the remnant of the extended primer can be determined by the mass of one or more of the fragments produced;

the composition of one or more of the fragments produced;

the length of one or more of the fragments produced;

the DNA sequence of one or more of the fragments produced, optionally using a method comprising use of next generation sequencing (NGS), single molecule real time (SMRT) sequencing, nanopore DNA sequencing, reversible terminated chemistry (for example, SOLEXA technology (Illumina)), combinatorial probe anchor synthesis (cPAS), mass spectrometry sequencing, or massively parallel signature sequencing (MPSS);

fluorescent or bioluminescent or equivalent methods, including changes in fluorescence polarization, an increase in fluorescence, for example, by detaching a quencher from a fluorescent or bioluminescent or equivalent moiety, The production of fluorescing or bioluminescent or equivalent fragments of interest may be determined by quantitative PCR (qPCR), digital PCR, or equivalents.

Sequencing Nucleic Acids

In alternative embodiments, provided are methods wherein the sequence of an amplicon, or a new extended DNA polynucleotide, is determined by DNA sequencing, optionally using method comprising use of next generation sequencing (NGS), single molecule real time (SMRT) sequencing, nanopore DNA sequencing, reversible termi-nated chemistry (for example, SOLEXA technology (Illu-mina)), combinatorial probe anchor synthesis (cPAS), mass spectrometry sequencing, or massively parallel signature sequencing (MPSS).

Any sequencing method known in the art can be used to sequence an amplicon, or a new extended DNA polynucle-otide, produced by a method as provided herein.

Products of Manufacture and Kits

Provided are products of manufacture and kits for prac-ticing methods as provided herein; and optionally, products of manufacture and kits can further comprise instructions for practicing methods as provided herein.

Any of the above aspects and embodiments can be combined with any other aspect or embodiment as disclosed here in the Summary, Figures and/or Detailed Description sections.

As used in this specification and the claims, the singular forms "a," "an" and "the" include plural referents unless the context clearly dictates otherwise.

Unless specifically stated or obvious from context, as used herein, the term "or" is understood to be inclusive and covers both "or" and "and".

Unless specifically stated or obvious from context, as used herein, the term "about" is understood as within a range of normal tolerance in the art, for example within 2 standard deviations of the mean. About can be understood as within 20%, 19%, 18%, 17%, 16%, 15%, 14%, 13%, 12% 11%, 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Unless specifically stated or obvious from context, as used herein, the terms "substantially all", "substantially most of", "substantially all of" or "majority of" encompass at least about 90%, 95%, 97%, 98%, 99% or 99.5%, or more of a referenced amount of a composition.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Incorporation by reference of these documents, standing alone, should not be construed as an assertion or admission that any portion of the contents of any document is considered to be essential material for satisfying any national or regional statutory disclosure requirement for patent applications. Notwithstanding, the right is reserved for relying upon any of such documents, where appropriate, for providing material deemed essential to the claimed subject matter by an examining authority or court.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The inven-tion illustratively described herein suitably may be practiced in the absence of any element(s) not specifically disclosed herein. Thus, for example, in each instance herein any of the terms "comprising", "consisting essentially of", and "con-sisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention. Embodiments of the invention are set forth in the following claims.

The invention will be further described with reference to the examples described herein; however, it is to be under-stood that the invention is not limited to such examples.

EXAMPLES

Unless stated otherwise in the Examples, all recombinant DNA techniques are carried out according to standard pro-tocols, for example, as described in Sambrook et al. (2012) Molecular Cloning: A Laboratory Manual, 4th Edition, Cold Spring Harbor Laboratory Press, NY and in Volumes 1 and 2 of Ausubel et al. (1994) Current Protocols in Molecular Biology, Current Protocols, USA. Other references for stan-dard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Back-ground to Bench, First Edition, Springer Verlag, Germany.

In alternative embodiments, the differences noted in the Examples is detected by sequencing, hybridization, mass spectrometry, fluorescence or bioluminesce or equivalent, electrophoresis, or any other technology that can detect changes in sequence, mass, composition, fragment length, fluorescence or bioluminesce, or fluorescence polarization, including those with nucleotide resolution.

Example 1: Detecting the Presence of a Target Sequence by an Unlabeled Primer-Based Reporter Assay This example describes and demonstrates the efficacy of exemplary methods as provided herein for detecting the presence of a specific nucleic acid by amplification of the sequence while simultaneously creating a reporter fragment that can be identified by a variety of means including its mass, composition, length, or sequence.

In alternative embodiments, exemplary methods as pro-vided herein comprise detecting a EGFR mRNA or fragment thereof. Referring to FIG. 1, after creating a first-strand complementary DNA (cDNA), a specific region is amplified using a first nucleic acid polynucleotide amplification primer where the 3' proximal sequence matches and is annealed to the target sequence and the 5' proximal sequence does not match the target sequence and contains one ribonucleotide residue (or RNA nucleotide). The first primer is extended by a DNA polymerase. Subsequently, the return primer binds to the extended first primer and is extended by a DNA poly-merase that copies over the RNA residue (i.e., inserting a dNMP coded for by the RNA nucleotide). Now in a double-stranded configuration, the RNA residue is cleaved on its 5' side by a thermostable RNase H2 enzyme (TS RNase H2), detaching a DNA fragment from the original, extended first nucleic acid polynucleotide amplification primer. The detached primer fragment may be detected by mass spectrometry or electrophoresis or other means. Since the extended return primer copied over the entirety of the first nucleic acid polynucleotide amplification primer, a new binding site for the first nucleic acid polynucleotide amplification primer is created and exponential amplification can proceed. The number of detached fragments increases with each round of amplification. The presence of the detached fragment indicates the presence of the target sequence.

A non-limiting example of a reverse transcriptase used to make the cDNA from an mRNA template that can be used to practice methods as provided herein is SUPERSCRIPT III™, a reverse transcriptase (ThermoFisher Scientific, cat. #18080085). Non-limiting examples of a proofreading DNA polymerase that can be used in methods as provided herein include the DNA polymerases: PHUSION HOT START II DNA POLYMERASE™ (ThermoFisher Scientific, cat. #F549L); Q5® HOT START HIGH-FIDELITY DNA POLYMERASE™ (New England Biolabs, cat. #M0493L); and PLATINUM SUPERFI II DNA POLYMERASE™ (ThermoFisher Scientific, cat. #12361050). A non-limiting example of a thermostable ribonuclease H2 that can be used in methods as provided herein is RNase H2 enzyme (IDT, cat. #11-03-02-03).

This exemplary method includes distinct advantages over current methods, including a shorter total target sequence since sufficient sequence between the amplification primers for the binding of a reporter sequence is not needed. When applied to the short pieces of DNA and RNA typical in liquid biopsy samples, this increases the detection rate.

Example 2: Detecting the Presence of an Allele-Specific Target Sequence by an Unlabeled Primer-Based Reporter Assay This example describes and demonstrates the efficacy of exemplary methods as provided herein for detecting the presence of a specific nucleic acid by amplification of the sequence while simultaneously creating a reporter fragment that can be identified by a variety of means including its mass, composition, length, or sequence.

In alternative embodiments, exemplary methods as provided herein comprise detecting a specific EGFR point mutation. Referring to FIG. 1, a specific DNA (or cDNA) region is amplified using an allele-specific first nucleic acid polynucleotide amplification primer where the 3' proximal sequence matches and is annealed to the target sequence comprising a specific allele, and the 5' proximal sequence does not match the target sequence and contains one ribonucleotide residue (or RNA nucleotide). The allele-specific first primer is extended by a DNA polymerase. Subsequently, the return primer binds to the extended first primer and is extended by a DNA polymerase that copies over the RNA residue (i.e., inserting a dNMP coded for by the RNA nucleotide). Now in a double-stranded configuration, the RNA residue is cleaved on its 5' side by a thermostable RNase H2 enzyme (TS RNase H2), detaching a DNA fragment from the original, extended first nucleic acid polynucleotide amplification primer. The detached primer fragment may be detected by mass spectrometry or electrophoresis or other means. Since the extended return primer copied over the entirety of the first nucleic acid polynucleotide amplification primer, a new binding site for the first nucleic acid polynucleotide amplification primer is created and exponential amplification can proceed. The number of detached fragments increases with each round of amplification. The presence of the detached fragment indicates the presence of the allele-specific target sequence.

Non-limiting examples of a DNA polymerase that can be used in methods as provided herein include HOT START TAQ™ DNA polymerase (New England Biolabs, cat. #M0495S), and TAQ™ DNA polymerase (ThermoFisher Scientific, cat. #EP0401). A non-limiting example of a thermostable ribonuclease H2 that can be used in methods as provided herein is RNase H2 enzyme (IDT, cat. #11-03-02-03).

This exemplary method includes distinct advantages over current methods, including a shorter total target sequence since sufficient sequence between the amplification primers for the binding of a reporter sequence is not needed. When applied to the short pieces of DNA and RNA typical in liquid biopsy samples, this increases the detection rate.

Example 3: Detecting the Presence of a Target Sequence by a Labeled Primer-Based Reporter Assay This example describes and demonstrates the efficacy of exemplary methods as provided herein for detecting the presence of a specific nucleic acid by amplification of the sequence while simultaneously creating a reporter that can be identified by means fluorescence or bioluminescent or equivalent.

In alternative embodiments, exemplary methods as provided herein comprise detecting a KRAS mRNA or fragment thereof. Referring to FIG. 2, after creating a first-strand complementary DNA (cDNA), a specific region is amplified using a first nucleic acid polynucleotide amplification primer where the 3' proximal sequence matches and is annealed to the target sequence and the 5' proximal sequence does not match the target sequence and contains one ribonucleotide residue (or RNA nucleotide) flanked by a fluorescence or bioluminescent or equivalent quencher (Q), in this example on the 5' side of the RNA residue and a fluorescent or bioluminescent or equivalent moiety (F), in this example on the 3' side of the RNA residue. The first primer is extended by a DNA polymerase. Subsequently, the return primer binds to the extended first primer and is extended by a DNA polymerase that copies over the RNA residue (i.e., inserting a dNMP coded for by the RNA nucleotide). Now in a double-stranded configuration, the RNA residue is cleaved on its 5' side by a thermostable RNase H2 enzyme (TS RNase H2), detaching a DNA fragment comprising the fluorescence quencher from the original, extended first nucleic acid polynucleotide amplification primer. The primer fragment that remains as part of the extended first nucleic acid polynucleotide amplification primer is now devoid of a fluorescence quencher and may be detected by fluorescence when suitably excited. Since the extended return primer copied over the entirety of the first nucleic acid polynucleotide amplification primer, a new binding site for the first nucleic acid polynucleotide amplification primer is created and exponential amplification can proceed. The number of primer fragments that remain as part of the extended first nucleic acid polynucleotide amplification primer increases with each round of amplification and may be detected by fluorescence when suitably excited now that the fluorescence quenchers have been detached. The fluorescence indicates the presence of the target sequence.

A non-limiting example of a reverse transcriptase used to make the cDNA from an mRNA template that can be used to practice methods as provided herein is SUPERSCRIPT™ III reverse transcriptase (ThermoFisher Scientific, cat. #18080085). Non-limiting examples of a proofreading DNA polymerase that can be used in methods as provided herein include PHUSION HOT START II DNA POLYMERASE™ (ThermoFisher Scientific, cat. #F549L); Q5® HOT START HIGH-FIDELITY DNA POLYMERASE™ (New England Biolabs, cat. #M0493L); and PLATINUM SUPERFI II DNA POLYMERASE™ (ThermoFisher Scientific, cat. #12361050). A non-limiting example of a thermostable ribonuclease H2 that can be used in methods as provided herein is RNase H2 enzyme (IDT, cat. #11-03-02-03).

This exemplary method includes distinct advantages over current methods, including a shorter total target sequence since sufficient sequence between the amplification primers for the binding of a reporter sequence is not needed. When applied to the short pieces of DNA and RNA typical in liquid biopsy samples, this increases the detection rate.

Example 4: Detecting the Presence of an Allele-Specific Target Sequence by a Labeled Primer-Based Reporter Assay This example describes and demonstrates the efficacy of exemplary methods as provided herein for detecting the presence of a specific nucleic acid by amplification of the sequence while simultaneously creating a reporter that can be identified by means of fluorescence.

In alternative embodiments, exemplary methods as provided herein comprise detecting a specific KRAS point mutation. Referring to FIG. 2, a specific DNA (or cDNA) region is amplified using an allele-specific first nucleic acid polynucleotide amplification primer where the 3' proximal sequence matches and is annealed to the target sequence comprising a specific allele, and the 5' proximal sequence does not match the target sequence and contains one ribonucleotide residue (or RNA nucleotide) flanked by a fluorescence quencher and a fluorescence emitter. The first primer is extended by a DNA polymerase. Subsequently, the return primer binds to the extended first primer and is extended by a DNA polymerase that copies over the RNA residue. Now in a double-stranded configuration, the RNA residue is cleaved on its 5' side by a thermostable RNase H2 enzyme (TS RNase H2), detaching a DNA fragment comprising the fluorescence quencher from the original, extended first nucleic acid polynucleotide amplification primer. The primer fragment that remains as part of the extended first nucleic acid polynucleotide amplification primer may be detected by fluorescence when suitably excited. Since the extended return primer copied over the entirety of the first nucleic acid polynucleotide amplification primer, a new binding site for the first nucleic acid polynucleotide amplification primer is created and exponential amplification can proceed. The number of primer fragments that remain as part of the extended first nucleic acid polynucleotide amplification primer increases with each round of amplification and may be detected by fluorescence when suitably excited now that the fluorescence quenchers have been detached. The fluorescence indicates the presence of the target sequence. FIG. 3 is a demonstration of this approach using qPCR.

Non-limiting examples of a DNA polymerase that can be used in methods as provided herein include HOT START TAQ™ DNA polymerase (New England Biolabs, cat. #M0495S), and TAQ™ DNA polymerase (ThermoFisher Scientific, cat. #EP0401). A non-limiting example of a thermostable ribonuclease H2 that can be used in methods as provided herein is RNase H2 enzyme (IDT, cat. #11-03-02-03).

This exemplary method includes distinct advantages over current methods, including a shorter total target sequence since sufficient sequence between the amplification primers for the binding of a reporter sequence is not needed. When applied to the short pieces of DNA and RNA typical in liquid biopsy samples, this increases the detection rate.

Example 5: Detecting the Presence of a Target Sequence by Primer-Based Fluorescence Polarization This example describes and demonstrates the efficacy of exemplary methods as provided herein for detecting the presence of a specific nucleic acid by amplification of the sequence while simultaneously creating a reporter fragment that can be identified by means of fluorescence polarization.

In alternative embodiments, exemplary methods as provided herein comprise detecting a PIK3CA mRNA or fragment thereof. Referring to FIG. 4, after creating a first-strand complementary DNA (cDNA), a specific region is amplified using a first nucleic acid polynucleotide amplification primer where the 3' proximal sequence matches and is annealed to the target sequence and the 5' proximal sequence does not match the target sequence and contains a fluorescent residue at its 5' end (or within a few nucleotides of the 5' end) with one ribonucleotide (or RNA nucleotide) near the 5' terminus but to the 3' side of the fluorescent residue. The first primer is extended by a DNA polymerase. Subsequently, the return primer binds to the extended first primer and is extended by a DNA polymerase that copies over the RNA residue (i.e., inserting a dNMP coded for by the RNA nucleotide). Now in a double-stranded configuration, the RNA residue is cleaved on its 5' side by a thermostable RNase H2 enzyme (TS RNase H2), detaching a DNA fragment comprising the fluorescent residue from the original, extended first nucleic acid polynucleotide amplification primer. The detached fragment retaining the fluorescent residue is significantly shorter than the original, first nucleic acid polynucleotide amplification primer and can be distinguished from it by a marked shift in fluorescence polarization. Since the extended return primer copied over the entirety of the first nucleic acid polynucleotide amplification primer, a new binding site for the first nucleic acid polynucleotide amplification primer is created and exponential amplification can proceed. The number of detached, fluorescent primer fragments increases with each round of amplification and may be detected by fluorescence polarization when suitably excited. The shift in fluorescence polarization indicates the presence of the target sequence.

A non-limiting example of a reverse transcriptase used to make the cDNA from an mRNA template that can be used to practice methods as provided herein is SUPERSCRIPT™ III™ reverse transcriptase (ThermoFisher Scientific, cat. #18080085). Non-limiting examples of a DNA polymerase that can be used in methods as provided herein include HOT START TAQ™ DNA polymerase (New England Biolabs, cat. #M0495S), and TAQ™ DNA polymerase (ThermoFisher Scientific, cat. #EP0401). Non-limiting examples of a proofreading DNA polymerase that can be used in methods as provided herein include PHUSION HOT START II™ DNA polymerase (ThermoFisher Scientific, cat. #F549L); Q5® HOT START HIGH-FIDELITY™ DNA polymerase (New England Biolabs, cat. #M0493L); DEEP VENT® DNA polymerase (New England Biolabs, cat. #M0258L) and PLATINUM SUPERFI II™ DNA polymerase (ThermoFisher Scientific, cat. #12361050). A non-limiting example of a thermostable ribonuclease H2 that can be used in methods as provided herein is RNase H2 enzyme (IDT, cat. #11-03-02-03).

This exemplary method includes distinct advantages over current methods, including a shorter total target sequence since sufficient sequence between the amplification primers for the binding of a reporter sequence is not needed. When applied to the short pieces of DNA and RNA typical in liquid biopsy samples, this increases the detection rate.

Example 6: Detecting the Presence of an Allele-Specific Target Sequence by Primer-Based Fluorescence Polarization This example describes and demonstrates the efficacy of exemplary methods as provided herein for detecting the presence of a specific nucleic acid by amplification of the sequence while simultaneously creating a reporter fragment that can be identified by means of fluorescence polarization.

In alternative embodiments, exemplary methods as provided herein comprise detecting a specific PIK3CA point mutation. Referring to FIG. 4, a specific DNA (or cDNA) region is amplified using an allele-specific first nucleic acid polynucleotide amplification primer where the 3' proximal sequence matches and is annealed to the target sequence and the 5' proximal sequence does not match the target sequence and contains a fluorescent residue at its 5' end (or within a few nucleotides of the 5' end) with one ribonucleotide (or RNA nucleotide) near the 5' terminus but to the 3' side of the fluorescent residue. The first primer is extended by a DNA polymerase. Subsequently, the return primer binds to the extended first primer and is extended by a DNA polymerase that copies over the RNA residue (i.e., inserting a dNMP coded for by the RNA nucleotide). Now in a double-stranded configuration, the RNA residue is cleaved on its 5' side by a thermostable RNase H2 enzyme (TS RNase H2), detaching a DNA fragment comprising the fluorescent residue from the original, extended first nucleic acid polynucleotide amplification primer. The detached fragment retaining the fluorescent residue is significantly shorter than the original, first nucleic acid polynucleotide amplification primer and can be distinguished from it by marked shift in fluorescence polarization. Since the extended return primer copied over the entirety of the first nucleic acid polynucleotide amplification primer, a new binding site for the first nucleic acid polynucleotide amplification primer is created and exponential amplification can proceed. The number of detached, fluorescent primer fragments increases with each round of amplification and may be detected by fluorescence polarization when suitably excited. The shift in fluorescence polarization indicates the presence of the target sequence.

A non-limiting example of a reverse transcriptase used to make the cDNA from an mRNA template that can be used to practice methods as provided herein is SUPERSCRIPT III™ reverse transcriptase (ThermoFisher Scientific, cat. #18080085). A non-limiting example of a thermostable ribonuclease H2 that can be used in methods as provided herein is RNase H2 enzyme (IDT, cat. #11-03-02-03).

This exemplary method includes distinct advantages over current methods, including a shorter total target sequence since sufficient sequence between the amplification primers for the binding of a reporter sequence is not needed. When applied to the short pieces of DNA and RNA typical in liquid biopsy samples, this increases the detection rate.

Example 7: Detecting the Presence of a Target Sequence by Primer Extension

This example describes and demonstrates the efficacy of exemplary methods as provided herein for detecting the presence of a specific nucleic acid by primer extension that subsequently creates a reporter fragment that can be identified by a variety of means including its mass, composition, length, or sequence.

In alternative embodiments, exemplary methods as provided herein comprise detecting a specific DNA sequence. Referring to FIG. 5, a primer with an optionally blocked 5' end has an RNA residue at its 3' terminus (ultimate position); at the penultimate position with a single DNA residue at its 3' terminus; at the antepenultimate position with two DNA residues at its 3' terminus; or at the preantepenultimate position with three DNA residues at its 3' terminus. None of these primers are a substrate for thermostable RNase H2 enzyme, which requires four (4) DNA residues to the 3' side of an RNA residue in order to cleave the RNA residue, which occurs at its 5' side. When annealed to a specific DNA sequence in the presence a DNA polymerase and dNTPs the primer annealed to its target is extended to where there are at least four (4) DNA residues to the 3' side of the RNA residue; the extended primer is now a substrate for thermostable RNase H2 enzyme, which cleaves the RNA residue at its 5' side. The fragments produced indicate the presence of the target sequence.

The assay can be configured so as to limit the extension of the primer to a fixed length by using one or more nucleotides that cannot be extended once incorporated, for example by using dideoxyribonucleotides. Referring again to FIG. 5, if the primer contains an RNA residue located at the preantepenultimate position with three DNA residues at its 3' terminus, then the addition of a single dideoxyribonucleotide to the 3' end of the primer results in a single base extension that makes the primer susceptible to cutting by the thermostable RNase H2 enzyme. The fragments are of specific length, mass, and composition, any of which can be used to indicate the presence of the target sequence. Note that if the primer is annealed immediately adjacent to a site where variants occur, that the mass and composition of the 3' fragment that results from the primer extension and cleavage by the thermostable RNase H2 enzyme will indicate the identity of the variant. Referring to FIG. 6, it can be seen that under certain circumstances that multiple fragments can be produced from a single target template. One such condition is thermal cycling that releases the fragments from their target template allowing for the binding of a full-length, unextended primer to bind which can be subsequently extended and cleaved. Another such condition is to run the reaction isothermally at a temperature where after annealing, extension, and cleavage of the primer occurs that the displacement of the resulting fragments by an uncleaved and unextended primer is thermodynamically favored and the process of extension, cleavage, and displacement is repeated.

The DNA target template can be prepared by a variety of means. A non-limiting example of a reverse transcriptase used to make the cDNA from an mRNA template that can be used to practice methods as provided herein is SUPER-SCRIPT III™ reverse transcriptase (ThermoFisher Scientific, cat. #18080085). Non-limiting examples of a DNA polymerase that can be used in methods as provided herein include HOT START TAQ™ DNA Polymerase (New England Biolabs, cat. #M0495S), and TAQ™ DNA polymerase (ThermoFisher Scientific, cat. #EP0401). Non-limiting examples of a proofreading DNA polymerase that can be used in methods as provided herein include PHUSION HOT START II™ DNA polymerase (ThermoFisher Scientific, cat. #F549L); Q5® HOT START HIGH-FIDELITY™ DNA polymerase (New England Biolabs, cat. #M0493L); DEEP VENT® DNA Polymerase (New England Biolabs, cat. #M0258L) and PLATINUM SUPERFI II™ DNA polymerase (ThermoFisher Scientific, cat. #12361050). A non-limiting example of a thermostable ribonuclease H2 that can be used in methods as provided herein is RNase H2 enzyme (IDT, cat. #11-03-02-03).

This exemplary method includes distinct advantages over current methods, including a higher level of stringency regarding template recognition since cleavage by the RNase H2 enzyme only occurs if the RNA residue is perfectly matched to the template and the primer is extended so that at least four (4) nucleotides are at the 3' side of the RNA residue.

Example 8: Detecting the Presence of a Target Sequence by Hybridization of an Unlabeled Probe This example describes and demonstrates the efficacy of exemplary methods as provided herein for detection by a first nucleic acid polynucleotide of a second nucleic acid polynucleotide (the target sequence) by hybridization and processing of the first nucleic acid polynucleotide probe to produce fragments the presence of which indicate the presence of the target sequence.

Referring to FIG. 7A, when a first nucleic acid polynucleotide with a single RNA residue is annealed to the target sequence to create a double-stranded configuration, the RNA residue is cleaved on the 5' side by thermostable RNase H2. The presence of either resulting fragment, i.e., the 5' fragment or the 3' fragment, indicates the presence of the target sequence. Detection of both fragments is also possible. Note that the RNA residue must be precisely matched to the target template or the cleavage will not take place; in this way, specific variants at the targeted nucleotide position can be detected. In a similar way, FIG. 7B illustrates a first nucleic acid polynucleotide with two RNA residues annealed to the target sequence. When annealed in a double-stranded configuration, the RNA residues are cleaved on their 5' sides. The presence of any of the resulting fragments, i.e., the 5' fragment or the 3' fragment or the internal fragment, indicates the presence of the target sequence. Detection of two or three fragments is also possible. Note that one of the RNA residues can be annealed to an invariant nucleotide and the cleavage at that RNA residue indicates that the target sequence is present; in addition, the other RNA residue can be annealed to a variant nucleotide and cleavage can only take place if this other RNA residue is base-paired to the variant nucleotide. Detection of the fragments indicates the presence of the target sequence with nucleotide resolution provided by the RNA residues. Analysis of the fragments by mass or length or sequence or composition provides the needed nucleotide resolution.

A non-limiting example of a thermostable ribonuclease H2 that can be used in methods as provided herein is RNase H2 enzyme (IDT, cat. #11-03-02-03).

This exemplary method includes distinct advantages over current methods, including a higher level of stringency regarding template recognition since cleavage by the RNase H2 enzyme only occurs if the RNA residue is perfectly matched to the template. Furthermore, a wider range of annealing temperatures is possible since the discrimination of variants is not based on small differences in Tus, but on the stringency of a perfect match provided by the RNase H2 enzyme. Additionally, it is possible to query multiple sites simultaneously by incorporating multiple RNA residues at different positions so that cleavage patterns are distinct and indicate which RNA residues were matched to the template and which were not.

Example 9: Detecting the Presence of a Target Sequence by Hybridization and Fluorescence Polarization This example describes and demonstrates the efficacy of exemplary methods as provided herein for detecting the presence of a specific nucleic acid target sequence by hybridization of a nucleic acid polynucleotide probe to the target under conditions where production of a reporter fragment that can be identified by means of fluorescence polarization indicates the presence of the target sequence.

In alternative embodiments, exemplary methods as provided herein comprise detecting a specific nucleic acid target sequence by hybridizing (or annealing) to the target a DNA polynucleotide probe that comprises one RNA residue with a fluor attached to the probe on the 3' side of the RNA residue(s). Referring to FIG. 8, when annealed in a double-stranded configuration, the one RNA residue is cleaved on the 5' side of the RNA residue by the action of an RNase H2 enzyme. The fluorescent moiety is now linked to a much smaller molecule than the original, intact nucleic acid polynucleotide probe. The fluorescence polarization signal of the smaller molecule decays faster than that of the original first primer, indicating the presence of the target sequence. The fluor could also be attached to the 5' end or attached internally as long as the portion of the cleaved probe that retains the fluorescent moiety yields a fluorescence polarization signal that is perceptively different from the original, intact nucleic acid polynucleotide probe. Detection of variants at a particular nucleotide position within the target sequence is possible by using multiple probes that differ in the identity of their RNA residue and that each specific RNA residue is matched to a specific fluorescent moiety. Identification of which fluorescent moiety yields a fluorescence polarization signal that is perceptively different from the original, intact nucleic acid polynucleotide probe serves to identify the variant.

The DNA target template can be prepared by a variety of means. A non-limiting example of a reverse transcriptase used to make the cDNA from an mRNA template that can be used to practice methods as provided herein is SUPERSCRIPT III™ reverse transcriptase (ThermoFisher Scientific, cat. #18080085). Non-limiting examples of a DNA polymerase that can be used in methods as provided herein include HOT START TAQ™ DNA polymerase (New England Biolabs, cat. #M0495S), and TAQ™ DNA Polymerase (ThermoFisher Scientific, cat. #EP0401). Non-limiting examples of a proofreading DNA polymerase that can be used in methods as provided herein include PHUSION HOT START II™ DNA polymerase (ThermoFisher Scientific, cat. #F549L); Q5® Hot Start High-Fidelity DNA polymerase (New England Biolabs, cat. #M0493L); Deep Vent® DNA polymerase (New England Biolabs, cat. #M0258L) and PLATINUM SUPERFI II™ DNA polymerase (ThermoFisher Scientific, cat. #12361050). A non-limiting example of a thermostable ribonuclease H2 that can be used in methods as provided herein is RNase H2 enzyme (IDT, cat. #11-03-02-03).

This exemplary method includes distinct advantages over current methods, including a higher level of stringency regarding template recognition since cleavage by the RNase H2 enzyme only occurs if the RNA residue is perfectly matched to the template. Furthermore, a wider range of annealing temperatures is possible since the discrimination of variants is not based on small differences in Tus, but on the stringency of a perfect match provided by the RNase H2 enzyme.

Example 10: Detecting the Presence of a Target Sequence by Hybridization of a Labeled Probe-Based Reporter This example describes and demonstrates the efficacy of exemplary methods as provided herein for detecting the presence of a specific nucleic acid target sequence by hybridization of a nucleic acid polynucleotide probe to the target under conditions where production of a reporter fragment that can be identified by means of increased fluorescence indicates the presence of the target sequence.

Referring to FIG. 9, a first nucleic acid polynucleotide is annealed to a target sequence. The first nucleic acid polynucleotide contains RNA residues flanked by a fluorescence quencher (Q), in this example on the 5' side of the RNA residue and a fluorescent moiety (F), in this example on the 3' side of the RNA residue. When annealed in a double-stranded configuration, the RNA residue is cleaved on the 5' side. The quencher and fluorescent moieties are no longer linked to each other and the fluorescence is enhanced. Detection of fluorescence indicates the presence of the target sequence. Detection of variants at a particular nucleotide position within the target sequence is possible by using multiple probes that differ in the identity of their RNA residue and that each specific RNA residue is matched to a specific fluorescent moiety. Identification of which fluorescent signal is enhance serves to identify the variant. Optionally, amplification of the target prior to hybridization may be performed.

The DNA target template can be prepared by a variety of means. A non-limiting example of a reverse transcriptase used to make the cDNA from an mRNA template that can be used to practice methods as provided herein is Super-Script™ III Reverse Transcriptase (ThermoFisher Scientific, cat. #18080085). Non-limiting examples of a DNA polymerase that can be used in methods as provided herein include HOT START TAQ™ DNA Polymerase (New England Biolabs, cat. #M0495S), and TAQ™ DNA polymerase (ThermoFisher Scientific, cat. #EP0401). Non-limiting examples of a proofreading DNA polymerase that can be used in methods as provided herein include PHUSION HOT START II™ DNA polymerase (ThermoFisher Scientific, cat. #F549L); Q5® HOT START HIGH-FIDELITY™ DNA polymerase (New England Biolabs, cat. #M0493L); DEEP VENT® DNA polymerase (New England Biolabs, cat. #M0258L) and PLATINUM SUPERFI II™ DNA polymerase (ThermoFisher Scientific, cat. #12361050). A non-limiting example of a thermostable ribonuclease H2 that can be used in methods as provided herein is RNase H2 enzyme (IDT, cat. #11-03-02-03).

This exemplary method includes distinct advantages over current methods, including a higher level of stringency regarding template recognition since cleavage by the RNase H2 enzyme only occurs if the RNA residue is perfectly matched to the template. Furthermore, a wider range of annealing temperatures is possible since the discrimination of variants is not based on small differences in Tus, but on the stringency of a perfect match provided by the RNase H2 enzyme.

Example 11: Exemplary Methods Using Allele-Specific Primers to Detect Low Target Nucleic Acid for Genotyping The data presented in this Example demonstrates the efficacy of methods as provided herein by presenting data generated by MALDI-TOF MS (matrix assisted laser desorption ionization-time of flight mass spectrometry (MALDI-TOF MS)) detection of nucleic acids generated using exemplary methods.

FIG. 10 illustrates data showing the utility of the method for genotyping using allele-specific primers and polymerase chain reaction (PCR):

Three single-nucleotide polymorphisms (SNPs) were examined. Each polymorphic site has two possible alleles, either a C nucleotide or a T nucleotide.

For each SNP assay three templates were examined: a CC homozygote; a TT homozygote; and a TC heterozygote.

For SNP01, the allele-specific primer for the C allele (10 ng or approximately 3,000 haploid genome equivalents of DNA was used) has a 5' moiety (the 5' tag) that does not match the target and contains a ribonucleotide that when in single-stranded form is not recognized and cleaved by the thermostable ribonuclease H2 (RNase H2, from Integrated DNA Technologies, Inc. Coralville, Iowa, USA) present in the PCR. When the C allele is present, the primer specific for the C allele is extended, the return primer binds to the extended allele-specific primer and copies over the extended C-specific primer, including the 5' tag, placing the ribonucleotide in the 5' tag into a double-stranded conformation. The ribonucleotide is recognized by the RNase H2 and is cleaved on its 5' side, releasing a single-stranded oligonucleotide of a specific mass that indicates the presence of the C allele template in the sample.

Also present in the PCR is an allele-specific primer for the T allele, however, the ribonucleotide present in the 5' tag is placed at a position that when cleaved releases a single-stranded oligonucleotide of a specific mass that differs from the oligonucleotide derived from the C-specific primer.

Following the PCR reaction samples are analyzed by MALDI-TOF Mass Spectrometry (Agena Bioscience, San Diego, CA, USA). As shown at the top of FIG. 10, labeled as SNP01: in the case of the sample that is homozygous for the C allele (CC), only an oligonucleotide of the mass appropriate for the fragment released from the C-specific primer is seen (marked by an arrow); in the case of the sample that is homozygous for the T allele (TT), only an oligonucleotide of the mass appropriate for the fragment released from the T-specific primer is seen (marked by an arrow); and in the case of the sample that is heterozygous (TC), oligonucleotides corresponding to both masses are observed (marked by two arrows).

Similar results are seen for genotyping assays for SNP02 and SNP03. Additional mass peaks are from other reaction products and do not pertain to the SNP assays shown here.

A number of embodiments of the invention have been described. Nevertheless, it can be understood that various modifications may be made without departing from the spirit and scope of the invention. Accordingly, other embodiments are within the scope of the following claims.

What is claimed is:

1. A method for detecting a target nucleic acid sequence, comprising:

(a) providing or having provided a sample, (b) providing or having provided a first synthetic nucleic acid polynucleotide primer, wherein the first synthetic nucleic acid polynucleotide primer comprises:

(i) nucleotide residues for base pairing pair or selectively binding or annealing to the target nucleic acid sequence under physiologic conditions, and (ii) one or more 5' nucleotide residues that are not complementary to the target nucleic acid;

(c) providing or having provided a DNA polymerase, and an exonuclease or endonuclease capable of recognizing the one or more 5' nucleotide residues of the first synthetic nucleic acid polynucleotide primer are not complementary to the target nucleic acid when incorporated in a double-stranded oligonucleotide, and based on this recognition the exonuclease or endonuclease cleaves the double-stranded oligonucleotide;

(d) contacting the first synthetic nucleic acid polynucleotide to the sample under conditions wherein the first synthetic nucleic acid polynucleotide is capable of annealing to the target nucleic acid;

(e) extending the length of the first synthetic nucleic acid polynucleotide primer in a 5' to 3' direction using the DNA polymerase using the target nucleic acid as a template, thereby generating an extended first synthetic nucleic acid polynucleotide primer;

(f) providing or having provided a reverse synthetic nucleic acid primer capable of binding or selectively annealing to the 3' end of the extended first synthetic nucleic acid polynucleotide primer, and binding or selectively annealing the reverse synthetic nucleic acid to the extended first synthetic nucleic acid polynucleotide primer;

(g) extending the length of the reverse synthetic nucleic acid in a 5' to 3' direction using the DNA polymerase using the extended synthetic nucleic acid polynucleotide primer as a template, and incorporating in the extended length the one or more 5' nucleotide residues that was not complementary to the target nucleic acid, thereby generating a double-stranded oligonucleotide comprising the one or more 5' nucleotide residues that was not complementary to the target nucleic acid; and (h) contacting the double-stranded oligonucleotide with the exonuclease or endonuclease, thereby cleaving or separating the one or more 5' nucleotide residues that was not complementary to the target nucleic acid from the double-stranded oligonucleotide, thereby generating one or more fragments of single-stranded nucleotide, wherein the generation or presence the one or more fragments of single stranded nucleotide indicates the presence of the target nucleic acid.

2. The method of claim 1, further comprising a step (i), comprising detecting presence of the one or more fragments of single-stranded nucleotide to detect or indicate the presence of the target nucleic acid.

3. The method of claim 1, wherein the one or more 5' nucleotide residues that are not complementary to the target nucleic acid on the synthetic nucleic acid polynucleotide primer comprise at least one ribonucleotide.

4. The method of claim 1, wherein the endonuclease is a non-sequence-specific endonuclease or an endonuclease that specifically cleaves an RNA: DNA hybrid oligonucleotide.

5. The method of claim 4, wherein the non-sequence-specific endonuclease is or comprises the activity of a ribonuclease H or ribonuclease H2.

6. The method of claim 1, where the one or more 5' nucleotide residues that do not match or are not complementary to the target nucleic acid on the synthetic nucleic acid polynucleotide primer comprise a damaged or modified nucleotide, and the endonuclease or the exonuclease removes the damaged or modified nucleotide.

7. The method of claim 1, where the one or more 5' nucleotide residues that de not match (or are not complementary to the target nucleic acid on the synthetic nucleic acid polynucleotide primer comprise a thymine glycol and the endonuclease is endonuclease VIII.

8. The method of claim 1, wherein when the synthetic nucleic acid polynucleotide primer is annealed to the target nucleic acid one or more or the 5' nucleotide residues that do not match or are not complementary to the target nucleic acid are base paired to the target nucleic acid, and the synthetic nucleic acid polynucleotide primer is cleaved by an endonuclease or exonuclease activity such that: both 5' and 3' fragments or the synthetic nucleic acid polynucleotide primer are produced, or, both 5' and 3' fragments of the synthetic nucleic acid polynucleotide primer are produced and one or more internal fragments of the synthetic nucleic acid polynucleotide primer are produced.

9. The method of claim 1, wherein the extended synthetic nucleic acid polynucleotide primer acts as a template in the amplification of the reverse synthetic nucleic acid primer, and as a consequence of the amplification the one or more unpaired residues of the one or more or the 5' nucleotide residues that are not complementary to the target nucleic acid are cleaved by an enzyme activity such that: 5' and 3' fragments are produced; and 5' and 3' fragments and one or more internal fragments are produced.

10. The method of claim 1, wherein the one or more cleavage fragments are detected by virtue of their: mass, composition, length, sequence and/or fluorescence.

11. The method of claim 1, wherein the amplification produces or generates one or more nucleic acid fragments that are proportional to the number of target nucleic acid polynucleotides present in the sample.

12. The method of claim 1, wherein the synthetic nucleic acid polynucleotide primer is or comprises an allele-specific primer.

13. The method of claim 1, wherein the amplification of only one allele is suppressed.

14. The method of claim 1, wherein the target nucleic acid is or comprises a complementary DNA created from an RNA template.

15. The method of claim 1, wherein an annealed synthetic nucleic acid polynucleotide primer is first extended by one or more nucleotides before a ribonucleic acid residue in the synthetic nucleic acid polynucleotide primer can be cleaved.

16. The method of claim 15, wherein the annealing and extension of the synthetic nucleic acid polynucleotide primer occurs at a temperature wherein if enzymatic cleavage at the ribonucleic acid residue occurs, displacement of resulting fragments by an uncleaved and unextended target nucleic acid polynucleotide is thermodynamically favored.

17. The method of claim 1, wherein the one or more 5' nucleotide residues that do not match or are not complementary to the target nucleic acid comprise a fluorescent moiety, or equivalent (F).

18. The method of claim 17, wherein the one or more 5' nucleotide residues that do not match or are not complementary to the target nucleic acid comprise a quencher molecule (Q), wherein the quencher molecule is capable of quenching or substantially lowering or dampening the signal of the fluorescent moiety, or equivalent (F) when the quencher molecule (Q) is in proximity, or within 1 to 20 nucleotide residues, or within 2 to about 40 or within 3 to about 50, or 4 to about 60 or more, of the fluorescent moiety, or equivalent (F), and the one or more 5' nucleotide residues between the quencher molecule (Q) and the fluorescent or bioluminescent moiety or equivalent (F) comprise a sequence recognized by an endonuclease or an exonuclease and cleaved when recognized by the endonuclease or the exonuclease.

19. The method of claim 17, wherein the quencher molecule (Q) molecule is positioned 5' or 3' to the fluorescent or bioluminescent moiety, or equivalent (F), in the one or more 5' nucleotide residues that are not complementary to the target nucleic acid, and a nuclease recognition site is interposed between the Q and F.

20. A method for detecting a target nucleic acid sequence, comprising:

(a) providing or having provided a sample comprising a target nucleic acid;

(b) providing or having provided a synthetic nucleic acid polynucleotide primer, wherein the synthetic nucleic acid polynucleotide primer comprises:

(i) sufficient nucleotide residues to base pair or selectively bind and anneal to the target nucleic acid sequence under physiologic conditions, and (ii) one or more 3' nucleotide residues that because of the proximity to the 3' end of the synthetic nucleic acid polynucleotide primer are not cleaved by an enzyme;

(c) providing or having provided a DNA polymerase, and an exonuclease or endonuclease capable of recognizing one or more 3' nucleotide residues of the synthetic nucleic acid polynucleotide primer, and based on the recognizing the exonuclease or endonuclease cleaves the double-stranded oligonucleotide;

(d) contacting the synthetic nucleic acid polynucleotide to the sample under conditions wherein the synthetic nucleic acid polynucleotide is capable of annealing to the target nucleic acid;

(e) extending the length of the synthetic nucleic acid polynucleotide primer in a 5' to 3' direction using the DNA polymerase using the target nucleic acid as a template, thereby generating an extended synthetic nucleic acid polynucleotide primer;

(f) contacting the double-stranded oligonucleotide with the exonuclease or endonuclease, thereby cleaving the sequence on the extended synthetic nucleic acid polynucleotide primer that was not initially recognized or cleavable by the endonuclease or exonuclease, thereby generating one or more fragments of single-stranded nucleotide, wherein the generation or presence the one or more fragments of single stranded-nucleotide indicates the presence of the target nucleic acid.

21. A method for detecting a target nucleic acid sequence, comprising:

(a) providing or having provided a sample comprising a target nucleic acid;

(b) providing or having provided a synthetic nucleic acid polynucleotide primer, wherein the synthetic nucleic acid polynucleotide primer comprises:

(i) sufficient nucleotide residues to base pair and selectively bind or anneal to the target nucleic acid sequence under physiologic conditions, and (ii) one or more 3' nucleotide residues that because of the proximity to the 3' end of the synthetic nucleic acid polynucleotide primer are not cleaved by an enzyme;

(c) providing or having provided a DNA polymerase, and an exonuclease or endonuclease capable of recognizing one or more 3' nucleotide residues of the synthetic nucleic acid polynucleotide primer, and based on the recognizing the exonuclease or endonuclease cleaves the double-stranded oligonucleotide;

(d) contacting the synthetic nucleic acid polynucleotide to the sample under conditions wherein the synthetic nucleic acid polynucleotide is capable of annealing to the target nucleic acid;

(e) extending the length of the synthetic nucleic acid polynucleotide primer in a 5' to 3' direction using the DNA polymerase using the target nucleic acid as a template, thereby generating an extended synthetic nucleic acid polynucleotide primer;

(f) contacting the double-stranded oligonucleotide with the exonuclease or endonuclease, thereby cleaving the sequence on the extended synthetic nucleic acid polynucleotide primer that was not initially recognized or cleavable by the endonuclease or exonuclease, thereby generating one or more fragments of single-stranded nucleotide, wherein the annealing and extension extending reaction conditions comprise a temperature where the cleaved and extended synthetic nucleic acid polynucleotide primer is displaced from the target nucleic acid by an unextended and uncleaved synthetic nucleic acid polynucleotide primer, in other words, the annealing and extension occurs at a temperature that thermodynamically favors binding of the uncleaved and unextended nucleic acid primer over the cleaved and extended primer, and the newly annealed uncleaved and unextended nucleic acid primer is extended in a 5' to 3' direction using the DNA polymerase using the target nucleic acid as a template, and again this extended nucleic acid primer can now be cleaved by the enzyme, thus generating additional cleaved primer fragments both 5' and 3' fragments, wherein the generation or presence the one or more 5' and/or 3' fragments of single-stranded nucleotide indicates the presence of the target nucleic acid.

22. The method of claim 1, wherein the biological sample comprises a target nucleic acid.

23. The method of claim 1, wherein the target nucleic acid comprises a cell free nucleic acid (cfNA).

24. The method of claim 1, wherein the nucleic acid (cfNA) comprises cell-free DNA (cfDNA) or a cell-free RNA (cfRNA), or a circulating cell-free DNA (ccfDNA) or a circulating cell-free RNA (ccfRNA), or an environmental DNA (eDNA) or an environmental RNA (eRNA).

25. The method of claim 1, wherein the sample comprises a biological sample.

26. The method of claim 20, wherein the sample comprises a biological sample.

27. The method of claim 21, wherein the sample comprises a biological sample.

28. The method of claim 21, wherein the synthetic nucleic acid polynucleotide primer is not extended the full 3' length of the target nucleic acid, or the synthetic nucleic acid polynucleotide primer is extended one to about 10, or two to about 20, or 3 to about 30, or about 4 to about 40, or more, nucleotide residues by the polymerase.

29. The method of claim 5, wherein the non-sequence-specific endonuclease is or comprises the activity of a thermostable ribonuclease H or a thermostable ribonuclease H2.

\* \* \* \* \*